US012767714B2

(12) United States Patent
Lin et al.

(10) Patent No.: US 12,767,714 B2
(45) Date of Patent: Oct. 20, 2026

(54) LAG-3 AND PD-1/LAG-3-ANTIBODIES

(71) Applicant: Eli Lilly and Company, Indianapolis, IN (US)

(72) Inventors: Yaqiong Lin, Carlsbad, CA (US); Marta Antonina Witek, Zionsville, IN (US); Jianghuai Xu, San Diego, CA (US)

(73) Assignee: Eli Lilly and Company, Indianapolis, IN (US)

(*) Notice: Subject to any disclaimer, the term of this patent is extended or adjusted under 35 U.S.C. 154(b) by 501 days.

(21) Appl. No.: 18/512,607

(22) Filed: Nov. 17, 2023

(65) Prior Publication Data

US 2024/0166745 A1 May 23, 2024

Related U.S. Application Data

(60) Provisional application No. 63/510,928, filed on Jun. 29, 2023, provisional application No. 63/384,260, filed on Nov. 18, 2022.

(51) Int. Cl.
*C07K 16/28* (2006.01)
*A61P 37/06* (2006.01)

(52) U.S. Cl.
CPC .......... *C07K 16/2803* (2013.01); *A61P 37/06* (2018.01); *C07K 16/2818* (2013.01); *C07K 2317/31* (2013.01); *C07K 2317/622* (2013.01); *C07K 2317/75* (2013.01)

(58) Field of Classification Search
CPC ............ C07K 16/2803; C07K 16/2818; C07K 2317/31; C07K 2317/622; C07K 2317/75; A61P 37/06
See application file for complete search history.

(56) References Cited

U.S. PATENT DOCUMENTS

2025/0197493 A1 6/2025 Balasubramaniam et al.

FOREIGN PATENT DOCUMENTS

WO 2017037203 A1 3/2017
WO 2018/153340 A1 8/2018
WO 2019/168745 9/2019
WO 2020/221928 A1 11/2020
WO 2020/247648 12/2020
WO 2023/178201 A2 9/2023

OTHER PUBLICATIONS

Dang, Xibei et al., "Epitope mapping of monoclonal antibodies: a comprehensive comparison of different technologies", MAES, vol. 15, No. 1, Nov. 27, 2023, p. 2285285.
Jiang, H. et al., "PD-L1/LAG-3 bispecific antibody enhances tumor-specific immunity", Oncoimmunology, 2021, vol. 10, No. 1, pp. 1-21.
Zhao, Qi, "Bispecific Antibodies for Autoimmune and Inflammatory Diseases: Clinical Progress to Date", BioDrugs (2020) 34:111-119.
Leaver-Fay, A. et al., "Computationally Designed Bispecific Antibodies using Negative State Repertoires," Structure, 2016; 24(4):641-651.
Wang, Jie et al. "A Phase i, Open-Label Study of MGD013, a Bispecific DART® Molecule Binding PD-1 and LAG-3 in Patients with Relapsed or Refractory Diffuse Large B-Cell Lymphoma" Blood, vol. 136, Suppl. 1, Nov. 2020, pp. 21-22.
Shi, et al., "Elevated serum autoantibodies against co-inhibitory PD-1 facilitate T cell proliferation and correlate with disease activity in new-onset systemic lupus erythematosus patients," Arthritis Research and Therapy, vol. 19, No. 52, pp. 1-10 (2017).
Mozaffarian, et al., "Active systemic lupus erythematosus is associated with failure of antigen-presenting cells to express programmed death ligand-1," Rheumatology, vol. 47, pp. 1335-1341 (2008).
Isakov, "Immune Checkpoint-Targeted Therapy: Cancer and Autoimmune Diseases Represent Two Sides of the Same Coin," J. Autoimmune Disorders, vol. 2, No. 2, p. 17 (2016).
Lecocq, et al., "The Next-Generation Immune Checkpoint LAG-3 and its Therapeutic Potential in Oncology: Third Time's a Charm," International Journal of Molecular Sciences, vol. 22, No. 1, p. 75 (2021).
Chocarro, et al., "Clinical landscape of LAG-3-targeted therapy," Immuno-Oncology and Technology; 2022: 14(c): 100079.doi: 10.1016/j.iotech.2022. 100079.
Angin, et al., "A LAG-3-Specific Agonist Antibody for the Treatment of T Cell-Induced Autoimmune Diseases," J. Immunol., vol. 204, No. 4, pp. 810-818 (2020).
Poirier, et el., "Antibody-mediated depletion of lymphocyte-activation gene-3 (LAG-3)-activated T lymphocytes prevents delayed-type hypersensitivity in non-human primates," Clinical & Experimental Immunology, vol. 164, pp. 265-274 (2011).

*Primary Examiner* — Gregory S Emch
*Assistant Examiner* — Estella M. Gustilo
(74) *Attorney, Agent, or Firm* — Quarles & Brady, LLP

(57) ABSTRACT

The present disclosure relates to antibodies that bind to and agonize human LAG-3, and to bispecific antibodies that bind to and agonize each of human PD-1 and human LAG-3.

34 Claims, No Drawings

Specification includes a Sequence Listing.

LAG-3 AND PD-1/LAG-3-ANTIBODIES

CROSS REFERENCE TO RELATED APPLICATIONS

This application claims priority to U.S. Provisional Application 63/384,260 filed Nov. 18, 2022 and 63/510,928 filed Jun. 29, 2023, the content of which is incorporated herein by reference in its entirety.

REFERENCE TO SEQUENCE LISTING SUBMITTED ELECTRONICALLY

The disclosure is being filed along with a Sequence Listing in ST.26 XML format. The Sequence Listing is provided as a file titled "30367_US.xml" created Jan. 19, 2024 and is 53892 bytes in size. The Sequence Listing information in the ST.26 XML format is incorporated herein by reference in its entirety.

FIELD OF THE INVENTION

The present disclosure is in the field of medicine. Particularly, the present disclosure relates to novel antibodies that agonize human LAG-3, and to novel bispecific antibodies agonize both human LAG-3 and human PD-1, compositions comprising such antibodies, and methods of using such antibodies for the treatment of autoimmune disease.

Immune checkpoint pathways modulate both the autoimmune response and the anti-cancer immune response (Isakov, N., *J. Autoimmune Disorders* 2016: 2(2): 17). In autoimmune disease therapy, promoting, i.e., agonizing, the effect of an immune-inhibitory pathway, such that the immune response is suppressed, is desirable. Conversely, in cancer therapy, inhibiting, i.e., antagonizing, the effect of an immune-inhibitory pathway, such that the immune response is stimulated, is desirable.

PD-1 is a type I cell membrane protein. Activation of the PD-1 pathway leads to inhibition of immune cell activation, such as reduced cellular proliferation, reduced cellular survival, and inhibition of inflammatory cytokines (e.g., IFNγ, TNFα and IL-2). PD-1 is expressed on recently activated immune cells, such as T cells, B cells, NKT cells, monocytes, and dendritic cells; and its expression is tightly regulated. The importance of PD-1 mediated signaling in modulating human immune response was demonstrated with the success of treating oncology patients with antagonist PD-1 antibodies. In addition, there are other known correlations between autoimmune disease activity and the PD-1 pathway (Mozaffarian, N., et al., 2008) and autoantibodies to PD-1 (Shi, H., et al., 2017). Human PD-1 agonist antibodies are known in the art (see, for example, WO 2019/168745 and WO 2020/247648).

LAG-3 (CD223) is a cell-surface inhibitory receptor. LAG-3 regulates T-cell effector functions, and LAG-3 antagonist therapies for cancer are being evaluated (Lecocq Q, et al., *Int. J. Molec. Sci.* 2021: 22(1): 75: Chocarro L, et al., *Immuno-Oncology and Technology* 2022; 14(C): 100079.doi: 10.1016/j.iotech.2022. 100079). PD-1/LAG-3 bispecific antagonist antibodies for the treatment of cancer have been disclosed. (Angin M, et al., *J. Immunol.* 2020; 204(4): 810-818). A LAG-3 agonist antibody has been disclosed (Angin M, et al., *J. Immunol.* 2020: 204(4): 810-818). However, it is believed that a PD-1/LAG-3 dual agonist bispecific antibody has not been previously reported.

There is no known therapy for treating autoimmune disease relating to a dual agonist antibody construct that binds human LAG-3 and does not deplete T-cells, agonizes the LAG-3 signaling pathway, binds human PD-1 and human LAG-3 with desirable association and dissociation rates for optimal agonist activity, agonizes each of the PD-1 and LAG-3 signaling pathways simultaneously, decreases T cell proliferation by promoting T-cell receptor signaling downregulation, instead of by depletion of T-cells, agonizes human PD-1 and human LAG-3 in an immunologically relevant context to achieve in vivo efficacy, exhibits an effect in vitro and/or in vivo that is greater than the effect of the combination of a human LAG-3 agonist antibody and a human PD-1 agonist antibody, displays sufficient potency as a bispecific molecule for the treatment and/or prevention of autoimmune disorders, and/or offers an effective alternative for drug switching when, during the treatment of an autoimmune disorder with another human PD-1 agonist antibody or human LAG-3 agonist antibody, therapy is suspended because of at least one adverse event and/or inefficacy (particularly, anti-drug antibody (ADA) mediated reduction in efficacy).

Accordingly, the present disclosure provides novel human LAG-3 agonist antibodies and novel human LAG-3/human PD-1 dual agonist bispecific antibodies.

The present disclosure provides an advance in the art by providing compositions and methods useful in the prevention, downregulation or amelioration of autoimmune and/or immune tolerance related disorders through immune checkpoint stimulation using an engineered human LAG-3/human PD-1 dual agonist bispecific antibody. The human LAG-3/human PD-1 dual agonist bispecific antibodies of the present disclosure may be capable of improving or restoring immune pathology, preferably, through inhibition of the adaptive arm of the immune response, abrogation of the antigen specific immune process and, thereby directly addressing the underlying disease pathology. The use of such antibodies clinically may lead to long-term durability or remission of the disease(s) being treated.

The preparation of bispecific molecules is generally known to be an unpredictable endeavor. For example, co-expressing two heavy chains and two light chains to generate an IgG bispecific antibody can result in some mis-assembly and unwanted byproducts (Lewis S M et al., *Nature Biotechnology* 2014; 32: 191-202: Leaver-Fay A, et al., *Structure* 2016; 24: 641-651). Thus, the present disclosure provides a human LAG-3/human PD-1 bispecific molecule that reduces Fc receptor binding, minimizes complement binding, minimizes oxidation, facilitates heteromab assembly, and is cross-reactive with human LAG-3 and human PD-1, and exhibits in vivo efficacy in at least one pre-clinical model of an autoimmune disorder.

The present disclosure provides an antibody that binds to human LAG-3, wherein the antibody comprises an antigen binding domain comprising a heavy chain variable region (VH) and a light chain variable region (VL), wherein the VH comprises heavy chain complementarity determining regions (HCDR): HCDR1 comprising SEQ ID NO: 1, HCDR2 comprising SEQ ID NO: 2, and HCDR3 comprising SEQ ID NO: 3; and the VL comprises light chain complementarity determining regions (LCDR): LCDR1 comprising SEQ ID NO: 4, LCDR2 comprising SEQ ID NO: 5, and LCDR3 comprising SEQ ID NO: 6.

In one preferred embodiment, the VH comprises SEQ ID NO: 13 and the VL comprises SEQ ID NO: 14.

In one preferred embodiment, the human LAG-3 antibody comprises a constant heavy (CH) region comprising SEQ ID NO: 15 and a constant light (CL) region comprising SEQ ID NO: 16.

In another preferred embodiment, the human LAG-3 antibody comprises a light chain (LC) comprising SEQ ID NO: 22, and a heavy chain (HC) comprising SEQ ID NO: 37, wherein X at position 328 in SEQ ID NO: 37 is a lysine residue or an alanine residue. In another preferred embodiment, X at position 328 in SEQ ID NO: 37 is a lysine residue. In another preferred embodiment, X at position 328 in SEQ ID NO: 37 is an alanine residue.

In another preferred embodiment, the human LAG-3 antibody comprises (a) an LC comprising SEQ ID NO: 22, and (b) an HC comprising SEQ ID NO: 21. In another preferred embodiment, the antibody comprises (a) an LC comprising SEQ ID NO: 22, and (b) an HC comprising SEQ ID NO: 31. In another preferred embodiment, the human LAG-3 antibody comprises an HC comprising SEQ ID NO: 21 and an LC comprising SEQ ID NO: 22.

The present disclosure also provides an antibody that binds to human LAG-3, wherein the antibody comprises an antigen binding domain comprising a VH and a VL,

- wherein the VH comprises heavy chain complementarity determining regions: HCDR1 comprising SEQ ID NO: 44, HCDR2 comprising SEQ ID NO: 45, and HCDR3 comprising SEQ ID NO: 47; and
- the VL comprises light chain complementarity determining regions: LCDR1 comprising SEQ ID NO: 48, LCDR2 comprising SEQ ID NO: 49, and LCDR3 comprising SEQ ID NO: 50.

In one preferred embodiment, the VH comprises SEQ ID NO: 53 and the VL comprises SEQ ID NO: 56.

In another preferred embodiment, the human LAG-3 antibody comprises a constant heavy CH region comprising SEQ ID NO: 58 and a CL region comprising SEQ ID NO: 60.

In another preferred embodiment, the human LAG-3 antibody comprises an LC comprising SEQ ID NO: 64, and an HC comprising SEQ ID NO: 61.

The present disclosure also provides an antibody that binds to human LAG-3, wherein the antibody comprises an antigen binding domain comprising a VH and a VL,

- wherein the VH comprises heavy chain complementarity determining regions: HCDR1 comprising SEQ ID NO: 51, HCDR2 comprising SEQ ID NO: 52, and HCDR3 comprising SEQ ID NO: 47; and
- the VL comprises light chain complementarity determining regions: LCDR1 comprising SEQ ID NO: 48, LCDR2 comprising SEQ ID NO: 49, and LCDR3 comprising SEQ ID NO: 50.

In one preferred embodiment, the VH comprises SEQ ID NO: 54 and the VL comprises SEQ ID NO: 56.

In another preferred embodiment, the human LAG-3 antibody comprises a CH region comprising SEQ ID NO: 58 and a CL region comprising SEQ ID NO: 60.

In another preferred embodiment, the human LAG-3 antibody comprises an LC comprising SEQ ID NO: 64, and an HC comprising SEQ ID NO: 62.

In another preferred embodiment, the human LAG-3 antibody is a human IgG1 or IgG4 isotype. In another preferred embodiment, the antibody is a human IgG1 isotype.

In another preferred embodiment, the antigen binding domain of the human LAG-3 is a single-chain variable fragment (scFv).

A lysine to alanine substitution in the Fc region of an antibody can be helpful in reducing ADCC and CDC. The present disclosure also provides a nucleic acid comprising a sequence encoding one or both of SEQ ID NO: 22 or SEQ ID NO: 37, wherein X at position 328 in SEQ ID NO: 37 is a lysine residue or an alanine residue. In one preferred embodiment. X at position 328 in SEQ ID NO: 37 is a lysine residue. In another preferred embodiment, X at position 328 in SEQ ID NO: 37 is an alanine residue. In another preferred embodiment, the present disclosure provides a vector comprising the nucleic acid.

In another preferred embodiment, the present disclosure provides a composition comprising a first vector comprising a nucleic acid sequence encoding SEQ ID NO: 22 and a second vector comprising a nucleic acid sequence encoding SEQ ID NO: 37, wherein X at position 328 in SEQ ID NO: 37 is a lysine residue or an alanine residue.

The present disclosure also provides a nucleic acid comprising a sequence encoding one or both of SEQ ID NO: 64 or SEQ ID NO: 61. The present disclosure also provides a nucleic acid comprising a sequence encoding one or both of SEQ ID NO: 64 or SEQ ID NO: 62.

In another preferred embodiment, the present disclosure provides a composition comprising a first vector comprising a nucleic acid sequence encoding SEQ ID NO: 64 and a second vector comprising a nucleic acid sequence encoding SEQ ID NO: 61.

In another preferred embodiment, the present disclosure provides a composition comprising a first vector comprising a nucleic acid sequence encoding SEQ ID NO: 64 and a second vector comprising a nucleic acid sequence encoding SEQ ID NO: 62.

In one preferred embodiment, the present disclosure provides a cell comprising the vectors. In another preferred embodiment, the present disclosure provides a cell comprising the composition. In another preferred embodiment, the cell is a mammalian cell. In another preferred embodiment, the cell or the mammalian cell is isolated. In another preferred embodiment, the present disclosure provides a process of producing an antibody comprising culturing the cell under conditions such that the antibody is expressed, and recovering the expressed antibody from the culture medium. In another preferred embodiment, the present disclosure provides an antibody produced by culturing the cell under conditions such that the antibody is expressed, and recovering the expressed antibody from the culture medium. In another preferred embodiment, the present disclosure provides composition comprising the human LAG-3 antibody of the invention.

The present disclosure also provides a pharmaceutical composition comprising the human LAG-3 antibody of the invention, and a pharmaceutically acceptable excipient, diluent or carrier. In one preferred embodiment the pharmaceutical composition comprises arginine.

The present disclosure also provides a pre-filled syringe a pharmaceutical composition comprising the human LAG-3 antibody of the invention, and a pharmaceutically acceptable excipient, diluent or carrier. In one preferred embodiment the pharmaceutical composition comprises arginine.

The present disclosure also provides a method of treating autoimmune disease in a subject in need thereof, comprising administering to the subject a therapeutically effective amount of the human LAG-3 antibody of the invention. In one preferred embodiment, the autoimmune disease is rheumatoid arthritis, ulcerative colitis, Type I diabetes mellitus, or systemic lupus erythematosus. In one preferred embodiment, the autoimmune disease is active disease. In another preferred embodiment, the autoimmune disease is in remission.

The present disclosure also provides the human LAG-3 antibody of the invention, for use in therapy.

The present disclosure also provides the human LAG-3 antibody of the invention, for use in the treatment of autoimmune disease. In a preferred embodiment, the autoimmune disease is rheumatoid arthritis, ulcerative colitis, Type I diabetes mellitus, or systemic lupus erythematosus. In one preferred embodiment, the autoimmune disease is active disease. In another preferred embodiment, the autoimmune disease is in remission.

The present disclosure also provides a pharmaceutical composition comprising the human LAG-3 antibody of the invention, for use in treating rheumatoid arthritis, ulcerative colitis, Type I diabetes mellitus, or systemic lupus erythematosus. In one preferred embodiment, the immune disease is active disease. In another preferred embodiment, the immune disease is in remission.

The present disclosure also provides the use of the human LAG-3 antibody of the invention, in the manufacture of a medicament for the treatment of rheumatoid arthritis, ulcerative colitis, Type I diabetes mellitus, or systemic lupus erythematosus.

The present disclosure also provides an antibody that binds to human PD-1, wherein the antibody comprises an antigen binding domain comprising a heavy chain variable region (VH) and a light chain variable region (VL), herein the VH comprises heavy chain complementarity determining regions (HCDR): HCDR1 comprising SEQ ID NO: 7, HCDR2 comprising SEQ ID NO: 8, and HCDR3 comprising SEQ ID NO: 9; and the VL comprises light chain complementarity determining regions (LCDR): LCDR1 comprising SEQ ID NO: 10, LCDR2 comprising SEQ ID NO: 11, and LCDR3 comprising SEQ ID NO: 12.

In one preferred embodiment, the human PD-1 antibody VH comprises SEQ ID NO: 17 and the VL comprises SEQ ID NO: 20.

In another preferred embodiment, the human PD-1 antibody comprises a constant heavy (CH) region comprising SEQ ID NO: 19 and a constant light region comprising SEQ ID NO: 20.

In another preferred embodiment, the human PD-1 antibody comprises a light chain (LC) comprising SEQ ID NO: 24, and a heavy chain (HC) comprising SEQ ID NO: 38, wherein X at position 328 in SEQ ID NO: 38 is a lysine residue or an alanine residue. In another preferred embodiment, X at position 328 in SEQ ID NO: 38 is a lysine residue. In another preferred embodiment, X at position 328 in SEQ ID NO: 38 is an alanine residue.

In another preferred embodiment, the human PD-1 antibody comprises (a) an LC comprising SEQ ID NO: 24, and (b) an HC comprising SEQ ID NO: 23. In another preferred embodiment, the antibody comprises (a) an LC comprising SEQ ID NO: 24, and (b) an HC comprising SEQ ID NO: 32. In another preferred embodiment, the human PD-1 antibody comprises a heavy chain comprising SEQ ID NO: 23 and a light chain comprising SEQ ID NO: 24.

In another preferred embodiment, the human PD-1 antibody VH comprises SEQ ID NO: 55 and the VL comprises SEQ ID NO: 57. In another preferred embodiment, the human PD-1 antibody comprises a constant heavy (CH) region comprising SEQ ID NO: 59 and a constant light region comprising SEQ ID NO: 20. In another preferred embodiment, the human PD-1 antibody comprises a light chain comprising SEQ ID NO: 65, and a heavy chain comprising SEQ ID NO: 63.

In another preferred embodiment, the human PD-1 antibody is a human IgG1 or IgG4 isotype. In another preferred embodiment, the antibody is a human IgG1 isotype.

In another preferred embodiment, the antigen binding domain of the human PD-1 is a single-chain variable fragment (scFv).

The present disclosure also provides a nucleic acid comprising a sequence encoding SEQ ID NO: 24 or SEQ ID NO: 38, wherein X at position 328 in SEQ ID NO: 38 is a lysine residue or an alanine residue. In one preferred embodiment, X at position 328 in SEQ ID NO: 38 is a lysine residue. In another preferred embodiment. X at position 328 in SEQ ID NO: 38 is an alanine residue. In another preferred embodiment, the present disclosure provides a vector comprising the nucleic acid.

In another preferred embodiment, the present disclosure provides a composition comprising a first vector comprising a nucleic acid sequence encoding SEQ ID NO: 24 and a second vector comprising a nucleic acid sequence encoding SEQ ID NO: 38, wherein X at position 328 in SEQ ID NO: 38 is a lysine residue or an alanine residue.

The present disclosure also provides a nucleic acid comprising a sequence encoding SEQ ID NO: 64 or SEQ ID NO: 62. In another preferred embodiment, the present disclosure provides a vector comprising the nucleic acid. In another preferred embodiment, the present disclosure provides a composition comprising a first vector comprising a nucleic acid sequence encoding SEQ ID NO: 64 and a second vector comprising a nucleic acid sequence encoding SEQ ID NO: 62.

In one preferred embodiment, the present disclosure provides a cell comprising the vectors. In another preferred embodiment, the present disclosure provides a cell comprising the composition. In another preferred embodiment, the cell is a mammalian cell. In another preferred embodiment, the cell or the mammalian cell is isolated. In another preferred embodiment, the present disclosure provides a process of producing an antibody comprising culturing the cell under conditions such that the antibody is expressed, and recovering the expressed antibody from the culture medium. In another preferred embodiment, the present disclosure provides an antibody produced by culturing the cell under conditions such that the antibody is expressed, and recovering the expressed antibody from the culture medium. In another preferred embodiment, the present disclosure provides composition comprising the human PD-1 antibody of the invention.

The present disclosure also provides a human LAG-3/human PD-1 dual agonist bispecific antibody, wherein the dual agonist antibody binds to each of human LAG-3 and human PD-1. In a preferred embodiment, the dual agonist binds to human LAG-3 and human PD-1 simultaneously. In another preferred embodiment, the dual agonist binds to human LAG-3 and human PD-1 simultaneously on the same T cell.

The present disclosure also provides a human LAG-3 agonist antibody that binds to an epitope on human LAG-3 comprising amino acid residues 183-202 of SEQ ID NO: 41 (human LAG-3). The present disclosure also provides a human LAG-3 agonist antibody that binds to an epitope on human LAG-3 comprising amino acid residues 203-225 of SEQ ID NO: 41. The present disclosure also provides a human LAG-3 agonist antibody that binds to an epitope on human LAG-3 comprising amino acid residues 183-202 of SEQ ID NO: 41 and amino acid residues 203-225 of SEQ ID NO: 41.

The present disclosure also provides a human LAG-3/human PD-1 dual agonist bispecific antibody, wherein the LAG-3 binding portion of the bispecific antibody binds to an epitope on human LAG-3 comprising amino acid residues 183-202 of SEQ ID NO: 41 (human LAG-3). The present disclosure also provides a human Lag-/human PD-1 dual agonist bispecific antibody, wherein the LAG-3 binding portion of the bispecific antibody binds to an epitope on human LAG-3 comprising amino acid residues 203-225 of SEQ ID NO: 41 (human LAG-3). The present disclosure also provides a human LAG-3/human PD-1 dual agonist bispecific antibody, wherein the LAG-3 binding portion of the bispecific antibody binds to an epitope on human LAG-3 comprising amino acid residues 183-202 of SEQ ID NO: 41 (human LAG-3) and amino acid residues 203-225 of SEQ ID NO: 41.

The present disclosure also provides a pharmaceutical composition comprising the human PD-1 antibody of the invention, and a pharmaceutically acceptable excipient, diluent or carrier.

The present disclosure also provides a method of treating autoimmune disease in a subject in need thereof, comprising administering to the subject a therapeutically effective amount of the human LAG-3/human PD-1 dual agonist bispecific antibody of the invention. In one preferred embodiment, the autoimmune disease is rheumatoid arthritis, ulcerative colitis, Type I diabetes mellitus, or systemic lupus erythematosus. In one preferred embodiment, the autoimmune disease is active disease. In another preferred embodiment, the autoimmune disease is in remission. In another preferred embodiment, the subject has been screened for the presence of LAG-3 and PD-1 on the same T cell or population of T cells. In another preferred embodiment, the subject has been identified as one in which LAG-3 and PD-1 are both present on the same T cell or population of T cells.

The present disclosure also provides the human LAG-3/human PD-1 dual agonist bispecific antibody of the invention, for use in therapy.

The present disclosure also provides the human LAG-3/human PD-1 dual agonist bispecific antibody of the invention, for use in the treatment of autoimmune disease. In a preferred embodiment, the autoimmune disease is rheumatoid arthritis, ulcerative colitis, Type I diabetes mellitus, or systemic lupus erythematosus. In one preferred embodiment, the autoimmune disease is active disease. In another preferred embodiment, the autoimmune disease is in remission.

The present disclosure also provides a pharmaceutical composition comprising the human LAG-3/human PD-1 dual agonist bispecific antibody of the invention, for use in treating rheumatoid arthritis, ulcerative colitis, Type I diabetes mellitus, or systemic lupus erythematosus. In one preferred embodiment, the immune disease is active disease. In another preferred embodiment, the immune disease is in remission.

The present disclosure also provides the use of the human LAG-3/human PD-1 dual agonist bispecific antibody of the invention, in the manufacture of a medicament for the treatment of rheumatoid arthritis, ulcerative colitis, Type I diabetes mellitus, or systemic lupus erythematosus.

Mutations are known to those of ordinary skill in the art that facilitate desired qualities. However, it cannot be predicted which, if any, or how many such mutations will facilitate the desired qualities of any particular monospecific antibody or bispecific antibody. The present invention provides antibodies that contain amino acid residue mutations that facilitate one or more of preferred bispecific antibody assembly, reduction or elimination C1q binding, reduction or elimination of non-specific and self-interaction, reduction of composition or formulation viscosity, elimination of deamidation residues, and reduction of immunogenicity.

In one preferred embodiment, the LAG-3/human PD-1 dual agonist bispecific antibody comprises the CDRs of a human LAG-3 agonist antibody of the invention (SEQ ID NOS: 1-6) and the CDRs of a human PD-1 agonist antibody. In another preferred embodiment, the LAG-3/human PD-1 dual agonist bispecific antibody comprises the CDRs of a human LAG-3 agonist antibody of the invention (SEQ ID NOS: 1-6) and the human PD-1 agonist antibody CDR sequences of SEQ ID NOS: 7-12.

In another preferred embodiment, the human LAG-3/human PD-1 dual agonist bispecific antibody comprises:

(a) a first antigen binding domain that binds human LAG-3 comprising a first heavy chain variable region (VH1) and a first light chain variable region (VL1), wherein the VH1 comprises: HCDR1 comprising SEQ ID NO: 1, HCDR2 comprising SEQ ID NO: 2, and HCDR3 comprising SEQ ID NO: 3; and wherein the VL1 comprises: LCDR1 comprising SEQ ID NO: 4, LCDR2 comprising SEQ ID NO: 5, and LCDR3 comprising SEQ ID NO: 6; and (b) a second antigen binding domain that binds human PD-1 comprising a second heavy chain variable region (VH2) and a second light chain variable region (VL2), wherein the VH2 comprises: HCDR1 comprising SEQ ID NO: 7, HCDR2 comprising SEQ ID NO: 8, and HCDR3 comprising SEQ ID NO: 9; and wherein the VL2 comprises LCDR1 comprising SEQ ID NO: 10, LCDR2 comprising SEQ ID NO: 11, and LCDR3 comprising SEQ ID NO: 12.

In one preferred embodiment, the VH1 comprises SEQ ID NO: 13 and the VL1 comprises SEQ ID NO: 14. In another preferred embodiment, the VH2 comprises SEQ ID NO: 17 and the VL2 comprises SEQ ID NO: 18.

In another preferred embodiment, the human LAG-3/human PD-1 dual agonist bispecific antibody comprises two heavy chains and two light chains, wherein the first heavy chain (HC1) comprises the first VH1 and a first heavy chain constant region, the first light chain (LC1) comprises the VL1 and a first light chain constant region, the second heavy chain (HC2) comprises the second VH2 and a second heavy chain constant region, and the second light chain (LC2) comprises the second VL2 and a second light chain constant region. In another preferred embodiment, the second light chain (LC2) comprises the VL2 and a second light chain constant region, wherein the HC1 is linked to the LC1 by an inter-chain disulfide bond, the HC2 is linked to the LC2 by an inter-chain disulfide bond, and the HC1 is linked to the HC2 by inter-chain disulfide bonds.

In another preferred embodiment, the HC1 comprises SEQ ID NO: 37, wherein X at position 328 in SEQ ID NO: 37 is lysine or alanine, the LC1 comprises SEQ ID NO: 22, the HC2 comprises SEQ ID NO: 38, wherein X at position 324 in SEQ ID NO: 38 is lysine or alanine, and the LC2 comprises SEQ ID NO: 24.

In another preferred embodiment. X at position 328 in SEQ ID NO: 37 is lysine, and X at position 324 in SEQ ID NO: 38 is lysine. In another preferred embodiment, X at position 328 in SEQ ID NO: 37 is alanine, and X at position 324 in SEQ ID NO: 38 is alanine.

In another preferred embodiment, the human LAG-3/human PD-1 dual agonist bispecific antibody comprises a first HC1 comprising SEQ ID NO: 21, a first LC1 comprising SEQ ID NO: 22, a second HC2 comprising SEQ ID NO: 23, and a second LC2 comprising SEQ ID NO: 24.

In another preferred embodiment, the human LAG-3/human PD-1 dual agonist bispecific antibody comprises a first HC1 comprising SEQ ID NO: 21, a first LC1 comprising SEQ ID NO: 22, a second HC2 comprising SEQ ID NO: 23, and a second LC2 comprising SEQ ID NO: 24.

In another preferred embodiment, the human LAG-3/human PD-1 dual agonist bispecific antibody comprises a first HC1 comprising SEQ ID NO: 31, a first LC1 comprising SEQ ID NO: 22, a second HC2 comprising SEQ ID NO: 32, and a second LC2 comprising SEQ ID NO: 24.

In another preferred embodiment, the human LAG-3/human PD-1 dual agonist bispecific antibody of the invention comprises a first constant heavy region (CH1) comprising SEQ ID NO: 15, a first constant light region (CL1) comprising SEQ ID NO: 16, a second constant heavy region (CH2) comprising SEQ ID NO: 19, and a second constant light region (CL2) comprising SEQ ID NO: 20.

In another preferred embodiment, the human LAG-3/human PD-1 dual agonist bispecific antibody of the invention comprises a CH1 comprising SEQ ID NO: 29, a CL1 comprising SEQ ID NO: 16, a CH2 comprising SEQ ID NO: 30, and a second constant light region (CL2) comprising SEQ ID NO: 20.

In another preferred embodiment, the first antigen binding domain of the bispecific antibody is an scFv, and the second antigen binding domain is an scFv.

The present disclosure also provides a nucleic acid comprising a sequence encoding one or more of SEQ ID NOS: 22, 24, 37, and 38, wherein X at position 328 in SEQ ID NO: 37 is a lysine residue or an alanine residue, wherein X at position 324 in SEQ ID NO: 38 is a lysine residue or an alanine residue, wherein if amino acid residue 328 in SEQ ID NO: 37 is a lysine residue, then X at position 324 in SEQ ID NO: 38 is a lysine residue, and wherein if X at position 328 in SEQ ID NO: 37 is an alanine residue, then X at position 324 in SEQ ID NO: 38 is an alanine residue.

The present disclosure also provides cell comprising a nucleic acid comprising a sequence encoding one more of the polypeptides of SEQ ID NOS: 22, 24, 37 and 38, wherein X at position 328 in SEQ ID NO: 37 is a lysine residue or an alanine residue, wherein amino acid residue 324 in SEQ ID NO: 38 is a lysine residue or an alanine residue, wherein if X at position 328 in SEQ ID NO: 37 is a lysine residue, then X at position 324 in SEQ ID NO: 38 is a lysine residue, and wherein if X at position 328 in SEQ ID NO: 37 is an alanine residue, then X at position 324 in SEQ ID NO: 38 is an alanine residue, and wherein the cell is capable of expressing the one or more polypeptides.

In another preferred embodiment of the LAG-3/human PD-1 dual agonist bispecific antibody of the invention, the LAG-3/human PD-1 dual agonist bispecific antibody comprises the CDRs of a human LAG-3 agonist antibody of the invention (SEQ ID NOS: 44, 45 and 4750)) and the CDRs of a human PD-1 agonist antibody. In another preferred embodiment, the LAG-3/human PD-1 dual agonist bispecific antibody comprises the CDRs of a human LAG-3 agonist antibody of the invention (SEQ ID NOS: 44, 45 and 47-50) and the human PD-1 agonist antibody CDR sequences of SEQ ID NOS: 7, 46 and 9-12.

In another preferred embodiment, the human LAG-3/human PD-1 dual agonist bispecific antibody comprises:

(a) a first antigen binding domain that binds human LAG-3 comprising a first VH1 and a first VL1, wherein the VH1 comprises: HCDR1 comprising SEQ ID NO: 44, HCDR2 comprising SEQ ID NO: 45, and HCDR3 comprising SEQ ID NO: 47; and wherein the VL1 comprises: LCDR1 comprising SEQ ID NO: 48, LCDR2 comprising SEQ ID NO: 49, and LCDR3 comprising SEQ ID NO: 50; and (b) a second antigen binding domain that binds human PD-1 comprising a second VH2 and a second VL2, wherein the VH2 comprises: HCDR1 comprising SEQ ID NO: 7, HCDR2 comprising SEQ ID NO: 46, and HCDR3 comprising SEQ ID NO: 9; and wherein the VL2 comprises LCDR1 comprising SEQ ID NO: 10, LCDR2 comprising SEQ ID NO: 11, and LCDR3 comprising SEQ ID NO: 12.

In another preferred embodiment, the human LAG-3/human PD-1 dual agonist bispecific antibody comprises a first HC1 comprising SEQ ID NO: 61, a first LC1 comprising SEQ ID NO: 64, a second HC1 comprising SEQ ID NO: 63, and a second LC1 comprising SEQ ID NO: 65.

In another preferred embodiment, the human LAG-3/human PD-1 dual agonist bispecific antibody comprises a first HC1 comprising SEQ ID NO: 62, a first LC1 comprising SEQ ID NO: 64, a second HC1 comprising SEQ ID NO: 63, and a second LC1 comprising SEQ ID NO: 65.

In another preferred embodiment, the first antigen binding domain of the bispecific antibody is an scFv, and the second antigen binding domain is an scFv.

The present disclosure also provides a nucleic acid comprising a sequence encoding one or more of SEQ ID NOS: 66, 68, 69 and 70. The present disclosure also provides cell comprising a nucleic acid comprising a sequence encoding one more of the polypeptides of SEQ ID 61, 63, 64 and 65.

The present disclosure also provides a nucleic acid comprising a sequence encoding one or more of SEQ ID NOS: 67-70. The present disclosure also provides cell comprising a nucleic acid comprising a sequence encoding one more of the polypeptides of SEQ ID 62-65.

In one preferred embodiment of the cell, the cell is a mammalian cell. In another preferred embodiment, the cell or the mammalian cell is isolated. In another preferred embodiment, the present disclosure provides a process of producing a human LAG-3/human PD-1 dual agonist antibody comprising culturing the cell under conditions such that the antibody is expressed, and recovering the expressed antibody from the culture medium. In another preferred embodiment, the present disclosure provides the human LAG-3/human PD-1 dual agonist antibody produced by culturing the cell under conditions such that the antibody is expressed, and recovering the expressed antibody from the culture medium.

The present disclosure also provides a pharmaceutical composition comprising the human LAG-3/human PD-1 dual agonist bispecific antibody of the invention, and a pharmaceutically acceptable excipient, diluent or carrier.

The present disclosure also provides a method of treating autoimmune disease in a subject in need thereof, comprising administering to the subject a therapeutically effective amount of the bispecific antibody of the invention. In one preferred embodiment, the autoimmune disease is rheumatoid arthritis, ulcerative colitis, Type I diabetes mellitus, or systemic lupus erythematosus. In another preferred embodiment, the autoimmune disease is active disease. In another preferred embodiment, the autoimmune disease is in remission. In another preferred embodiment, the human LAG-3/human PD-1 dual agonist bispecific antibody exhibits an effect in vitro and/or in vivo that is greater than the effect of the combination of the corresponding monospecific human LAG-3 agonist antibody and corresponding monospecific human PD-1 antibody.

The present disclosure also provides the human LAG-3/human PD-1 dual agonist bispecific antibody of the invention, for use in therapy.

The present disclosure also provides the human LAG-3/human PD-1 dual agonist bispecific antibody of the invention, for use in the treatment of autoimmune disease. In a preferred embodiment, the autoimmune disease is rheumatoid arthritis, ulcerative colitis, Type I diabetes mellitus, or systemic lupus erythematosus. In one preferred embodiment, the autoimmune disease is active disease. In another preferred embodiment, the autoimmune disease is in remission.

The present disclosure also provides a pharmaceutical composition comprising the human LAG-3/human PD-1 dual agonist bispecific antibody of the invention, for use in treating autoimmune disease. In a preferred embodiment, the autoimmune disease is rheumatoid arthritis, ulcerative colitis, Type I diabetes mellitus, or systemic lupus erythematosus. In another preferred embodiment, the immune disease is active disease. In another preferred embodiment, the immune disease is in remission.

The present disclosure also provides the use of the human LAG-3/human PD-1 dual agonist bispecific antibody of the invention, in the manufacture of a medicament for the treatment of rheumatoid arthritis, ulcerative colitis, Type I diabetes mellitus, or systemic lupus erythematosus. In one preferred embodiment, the immune disease is active disease. In another preferred embodiment, the immune disease is in remission.

In embodiments that refer to a method of treatment as described herein, such embodiments are also further embodiments for use in that treatment, or alternatively for the use in the manufacture of a medicament for use in that treatment.

In one preferred embodiment, the human LAG-3 antibody of the invention or the human LAG-3/human PD-1 dual agonist bispecific antibody of the invention is substantially pure. In another preferred embodiment, the human LAG-3 antibody of the invention or the human LAG-3/human PD-1 dual agonist bispecific antibody of the invention is sterile.

The term "autoimmune disease" as used herein refers to undesirable conditions that arise from an inappropriate or unwanted immune reaction against self-cells and/or tissues or transplanted cells and/or tissues. The term "autoimmune disease" is meant to include such conditions, whether they be mediated by humoral or cellular immune responses. Exemplary autoimmune diseases or disorders include, but are not limited to, graft-versus-host disease (GVHD), solid organ transplantation rejection, vasculitis, systemic lupus erythematosus (SLE), type 1 diabetes mellitus (TIDM), multiple sclerosis (MS), giant cell arteritis (GCA), psoriasis (PsO), psoriatic arthritis (PSA), rheumatoid arthritis (RA), inflammatory bowel disease (IBD), ulcerative colitis (UC), ankylosing spondylitis (AS), Sjogren's syndrome (SjS), autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's. Wegener's granulomatosis, myocarditis, myositis, polymyalgia rheumatic (PMR), spontaneous abortion, vitiligo, atherosclerosis, autoimmune pancreatitis, bullous pemphigoid, chronic viral infections, and myasthenia gravis. For purposes of the present disclosure, preferred autoimmune diseases are graft-versus-host disease (GVHD), solid organ transplantation rejection, vasculitis, systemic lupus erythematosus (SLE), type 1 diabetes mellitus (TIDM), multiple sclerosis (MS), giant cell arteritis (GCA), psoriasis (PsO), psoriatic arthritis (PSA), rheumatoid arthritis (RA), inflammatory bowel disease (IBD), ulcerative colitis (UC), ankylosing spondylitis (AS), Sjogren's syndrome (SjS), autoimmune hepatitis, and scleroderma.

In a preferred embodiment, the immune disease is rheumatoid arthritis, ulcerative colitis, Type I diabetes mellitus, or systemic lupus erythematosus. In another preferred embodiment, the immune disease is rheumatoid arthritis. In another preferred embodiment, the immune disease is ulcerative colitis. In another preferred embodiment, the immune disease is Type I diabetes mellitus. In another preferred embodiment, the immune disease is systemic lupus erythematosus. In another preferred embodiment, the immune disease is active disease. In another preferred embodiment, the immune disease is in remission.

In another preferred embodiment, a human LAG-3/human PD-1 dual agonist bispecific antibody of the invention binds human LAG-3, but does not deplete T-cells.

In another preferred embodiment, a human LAG-3/human PD-1 dual agonist bispecific antibody of the invention agonizes the LAG-3 signaling pathway.

In another preferred embodiment, a human LAG-3/human PD-1 dual agonist bispecific antibody of the invention binds human PD-1 and human LAG-3 with desirable association and dissociation rates for optimal agonist activity.

In another preferred embodiment, a human LAG-3/human PD-1 dual agonist bispecific antibody of the invention agonizes each of the PD-1 and LAG-3 signaling pathways simultaneously.

In another preferred embodiment, a human LAG-3/human PD-1 dual agonist bispecific antibody of the invention decreases T cell proliferation by promoting T-cell receptor signaling downregulation, instead of by depletion of T-cells.

In another preferred embodiment, a human LAG-3/human PD-1 dual agonist bispecific antibody of the invention agonizes human PD-1 and human LAG-3 in an immunologically relevant context to achieve in vivo efficacy In another preferred embodiment, a human LAG-3/human PD-1 dual agonist bispecific antibody of the invention exhibits an effect in vitro and/or in vivo that is greater than the effect of the combination of a human LAG-3 agonist antibody and a human PD-1 agonist antibody.

The present disclosure also provides a method comprising: (a) contacting a human LAG-3/human PD-1 dual agonist bispecific antibody of the invention with cells that express the extracellular domain of human PD-1 fused to an enzyme acceptor subunit of a reporter gene and the extracellular domain of human LAG-3 fused to an enzyme donor subunit: (b) incubating the contacted cells under conditions suitable for the bispecific antibody to bind to the extracellular domain of human PD-1 and to the extracellular domain of human LAG-3: (c) contacting the cells with a reporter compound; (d) assaying the amount of reporter compound; and (e) determining an IC50 for the bispecific antibody binding to the cells. In one preferred embodiment, the enzyme acceptor subunit of the reporter gene is beta-galactosidase, and the enzyme donor subunit is PKI enzyme donor subunit of beta-galactosidase. In another preferred embodiment, the bispecific antibody comprises 1) the heavy chain (HC) of SEQ ID NO: 21 and the light chain (LC) of SEQ ID NO: 22, and 2) the HC of SEQ ID NO: 23 and the LC of SEQ ID NO: 24. In another preferred embodiment, the bispecific antibody comprises: 1) the HC of SEQ ID NO: 31 and the LC of SEQ ID NO: 22, and 2) the HC of SEQ ID NO: 32 and the LC of SEQ ID NO: 24. In another preferred embodiment, the bispecific antibody comprises 1) the HC of SEQ ID NO: 61 and the LC of SEQ ID NO: 64, and 2) the HC of SEQ ID NO: 63 and the LC of SEQ ID NO: 65. In another preferred embodiment, the bispecific antibody comprises 1) the HC of SEQ ID NO: 62 and the LC of SEQ ID NO: 64, and 2) the HC of SEQ ID NO: 63 and the LC of SEQ ID NO: 65.

As used herein "PD-1" refers to programmed cell death 1, also known as programmed death 1 (PD-1; CD279), a type I cell membrane protein that belongs to the extended CD28/CTLA-4 family containing an extracellular IgV domain followed by a transmembrane and intracellular domain.

As used herein "hPD-1" or "human PD-1" refers to a wild-type human PD-1, for example, a wild-type human PD-1 that has the amino acid sequence set forth in SEQ ID NO: 39 (i.e., NCBI Reference Sequence NP_005009.2).

A PD-1 polypeptide "extracellular domain" or "ECD" refers to a form of the PD-1 polypeptide that is essentially free of the transmembrane and cytoplasmic domains. Preferably, a PD-1 ECD has less than 1% of the transmembrane and cytoplasmic domain, more preferably, a PD-1 ECD has less than 0.5% of such domains. Even more preferably, human PD-1 ECD polypeptide is as shown in SEQ ID NO: 40. PD-1 polypeptide ECD may be prepared using methods known in the art. Alternatively, human PD-1 polypeptide ECD may be purchased commercially from various vendors such as Sino Biological (Beijing, China: reference #10377-H08) and R&D Systems (Minneapolis, MN, USA: cat. #8986-PD).

As used herein "LAG-3" refers to lymphocyte activation gene 3, also known as CD223, which belongs to the immunoglobulin superfamily. The terms LAG-3, LAG3, Lag-3 and Lag3 are synonymous.

As used herein "hLAG-3" or "human LAG-3" refers to a wild-type human LAG-3, preferably, a wild-type human LAG-3 that has the amino acid sequence set forth in SEQ ID NO: 41 (i.e., NCBI Reference Sequence NP_002277).

A LAG-3 polypeptide "extracellular domain" or "ECD" refers to a form of the LAG-3 polypeptide that is essentially free of the transmembrane and cytoplasmic domains. Preferably, a LAG-3 ECD has less than 1% of the transmembrane and cytoplasmic domain, more preferably, a LAG-3 ECD has less than 0.5% of such domains. Even more preferably, human LAG-3' ECD polypeptide is as shown in SEQ ID NO: 42. LAG-3 polypeptide ECD may prepared using methods known in the art. Alternatively, human LAG-3 polypeptide ECD may be purchased commercially from various vendors such as Bertyn Bioreagent (Rockville, MD, USA, Cat. No. 32083).

As used herein, "human PD-1 agonist antibody" refers to an antibody that binds to human PD-1, and, when administered in vivo, results in at least one significantly lessened autoimmune activity, such as reduction in anti-double stranded DNA (ds-DNA) titers, reduction in disease scores or reduction in inflammatory cytokines.

As used herein, "human LAG-3 agonist antibody" refers to an antibody that binds to human LAG-3, and, when administered in vivo, results in at least one significantly lessened autoimmune activity, such as reduction in anti-double stranded DNA (ds-DNA) titers, reduction in disease scores or reduction in inflammatory cytokines. In one preferred embodiment, the LAG-3 agonist antibody is "Antibody E," which refers to a human LAG-3 binding agonist antibody with the HC of SEQ ID NO: 21 and the LC of SEQ ID NO: 22.

In another preferred embodiment, the LAG-3 agonist antibody is variant of Antibody E, which is an antibody with the HC of SEQ ID NO: 31 and the LC of SEQ ID NO: 22.

In another preferred embodiment, the LAG-3 agonist antibody is "Antibody F." which refers to a human LAG-3 binding agonist antibody with the HC of SEQ ID NO: 61 and the LC of SEQ ID NO: 64.

In another preferred embodiment, the LAG-3 agonist antibody is variant of Antibody F, which is an antibody with the HC of SEQ ID NO: 62 and the LC of SEQ ID NO: 64.

In another preferred embodiment, the LAG-3 agonist antibody is variant of Antibody F referred to herein as "Antibody G." which is an antibody with the HC of SEQ ID NO: 61 having a serine to histidine substitution at amino acid reside 30 and a threonine to serine substitution at amino acid residue 61, and the LC of SEQ ID NO: 64.

As used herein, a "human LAG-3/human PD-1 dual agonist antibody" refers to an antibody comprising the CDR sequences of (a) SEQ ID NOS: 1-12, or (b) SEQ ID NOS: 44, 45 and 47-50) and 7, 46 and 9-12. In a preferred embodiment, the dual agonist antibody comprises 1) the variable heavy (VH) sequence of SEQ ID NO: 13 and the variable light (VL) sequence of SEQ ID NO: 14, and 2) the VH sequence of SEQ ID NO: 17 and the VL sequence of SEQ ID NO: 18. In another preferred embodiment, the dual agonist antibody is "Antibody A." which refers to a human PD-1 binding and human LAG-3 binding dual agonist antibody with: 1) the HC of SEQ ID NO: 21 and the LC of SEQ ID NO: 22, and 2) the HC of SEQ ID NO: 23 and the LC of SEQ ID NO: 24. In another preferred embodiment, the dual agonist antibody is "Antibody B." refers to a human PD-1 binding and human LAG-3 binding antibody with: 1) the HC of SEQ ID NO: 31 and the LC of SEQ ID NO: 22, and 2) the HC of SEQ ID NO: 32 and the LC of SEQ ID NO: 24. Antibodies A and B bind to the same epitope on human LAG-3.

In another preferred embodiment, the dual agonist antibody comprises 1) the variable heavy VH sequence of SEQ ID NO: 53 and the variable light VL sequence of SEQ ID NO: 56, and 2) the VH sequence of SEQ ID NO: 55 and the VL sequence of SEQ ID NO: 57. In another preferred embodiment, the dual agonist antibody is "Antibody C." which refers to a human PD-1 binding and human LAG-3 binding dual agonist antibody with: 1) the HC of SEQ ID NO: 61 and the LC of SEQ ID NO: 64, and 2) the HC of SEQ ID NO: 63 and the LC of SEQ ID NO: 65. Antibodies C and D bind to the same epitope on human LAG-3, which is different than the epitope on human LAG-3 to which antibodies A and B bind.

In a preferred embodiment, the dual agonist antibody comprises 1) the variable heavy VH sequence of SEQ ID NO: 54 and the variable light VL sequence of SEQ ID NO: 56, and 2) the VH sequence of SEQ ID NO: 55 and the VL sequence of SEQ ID NO: 57. In another preferred embodiment, the dual agonist antibody is "Antibody D," which refers to a human PD-1 binding and human LAG-3 binding dual agonist antibody with: 1) the HC of SEQ ID NO: 62 and the LC of SEQ ID NO: 64, and 2) the HC of SEQ ID NO: 63 and the LC of SEQ ID NO: 65.

It is believed that the anti-human LAG-3/anti-human PD-1 dual agonist molecules, e.g., dual agonist bispecific antibodies, disclosed herein are the first such dual agonist molecules to be disclosed.

It is also believed that the disclosure herein is the first report of a T cell population that contains both the human LAG-3 target protein and the PD-1 target protein on the same T cell. It is also believed that the disclosure herein is the first report that human LAG-3 is expressed more highly on CD8+ T cells than on CD4+ T cells, and that human PD-1 is expressed more highly on CD4+ T cells than on CD8+ T cells. It is also believed that the disclosure herein is the first report of a T cell population that contains a higher concentration of the human PD-1 target protein than the concentration of the human LAG-3 target protein on the same T cell. In one preferred embodiment, the ratio of PD-1 protein to LAG-3 protein on the surface of a T cell is about 2:1, about 2.5:1, about 3:1, about 3.5:1, about 4:1, about 4.5:1, about 5:1, about 5.5:1, or about 6:1. In another preferred embodiment, the ratio of PD-1 protein to LAG-3 protein on the surface of a T cell is about 3:1 to about 5:1.

The term "antibody." as used herein, refers to an immunoglobulin molecule that binds an antigen. Embodiments of an antibody include a monoclonal antibody, polyclonal antibody, human antibody, humanized antibody, chimeric antibody, bispecific or multispecific antibody, or conjugated antibody. The antibodies can be of any class (e.g., IgG, IgE, IgM, IgD, IgA), and any subclass (e.g., IgG1, IgG2, IgG3, IgG4). In a preferred embodiment, the antibody or bispecific antibody of the invention is an IgG1.

An exemplary antibody of the present disclosure is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org: see Lefranc et al., Nucleic Acids Res. 1999; 27:209-212). In the disclosure herein, the Kabat method is used to assign amino acid residues to the CDRs.

Embodiments of the present disclosure also include antibody fragments or antigen-binding fragments that, as used herein, comprise at least a portion of an antibody retaining the ability to specifically interact with an antigen or an epitope of the antigen, such as Fab, Fab', $F(ab')_2$. Fv fragments, scFv antibody fragments, scFab, disulfide-linked Fvs (sdFv), a Fd fragment.

The term "antigen binding domain", as used herein, refers to a portion of a that binds an antigen or an epitope of the antigen. For example, the antigen binding domain in the human LAG-3 antibody of the invention binds to human LAG-3 (SEQ ID NO: 41) or to a fragment thereof, e.g., LAG-3 ECD (SEQ ID NO: 42). The bispecific antibody of the invention comprises two antigen-binding domains, one of which binds to human LAG-3 (SEQ ID NO: 41) or to a fragment thereof, e.g., LAG-3 ECD (SEQ ID NO: 42), and the other of which binds to binds to human PD-1 (SEQ ID NO: 39) or to a fragment thereof, e.g., PD-1 ECD (SEQ ID NO: 40)).

The term "bispecific", as used herein, refers to a molecule that comprises two distinct antigen-binding domains. A bispecific binding molecule can bind two different antigens or two different epitopes of the same antigen. Exemplary embodiments of bispecific molecules include the bispecific antibodies disclosed herein.

The term "agonize", as used herein, refers to the ability of an antibody, antibody fragment, or a binding molecule to induce or increase one or more activities or functions associated with an antigen.

Preferably, antibodies of the present disclosure contain a Fc portion which is a human IgG1 subtype. It is well-known that human IgG1 binds to the Fc-gamma receptor family (FcγR) as well as C1q. Interaction with these receptors can induce antibody-dependent cell cytotoxicity (ADCC) and complement-dependent cytotoxicity (CDC). In a preferred embodiment, the monoclonal anti-human LAG-3 antibody of the invention does not exhibit substantial ADCC activity. In another preferred embodiment, the monoclonal anti-human LAG-3 antibody of the invention does not exhibit ADCC activity. In another preferred embodiment, the anti-human LAG-3/anti-human PD-1 dual agonist bispecific antibody of the invention does not exhibit substantial ADCC activity. In another preferred embodiment, the anti-human LAG-3/anti-human PD-1 dual agonist bispecific antibody of the invention does not exhibit ADCC activity.

In a preferred embodiment, the monoclonal anti-human LAG-3 antibody of the invention does not substantially deplete T cells. In another preferred embodiment, the monoclonal anti-human LAG-3 antibody of the invention does not deplete T cells. In another preferred embodiment, the anti-human LAG-3/anti-human PD-1 dual agonist bispecific antibody of the invention does not substantially deplete T cells. In another preferred embodiment, the anti-human LAG-3/anti-human PD-1 dual agonist bispecific antibody of the invention does not deplete T cells.

An isolated DNA encoding a CH region can be converted to a full-length heavy chain gene by operably linking the VH-encoding DNA to another DNA molecule encoding heavy chain constant regions. The sequences of human, as well as other mammalian, heavy chain constant region genes are known in the art. DNA fragments encompassing these regions can be obtained, e.g., by standard PCR amplification.

An isolated DNA encoding a VL region may be converted to a full-length light chain gene by operably linking the VL-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. In one preferred embodiment, the light chain constant region of an anti-LAG-3 antibody of the invention is a kappa constant region. In another preferred embodiment, for an anti-LAG-3/anti-PD-1 dual agonist antibody of the invention, the light chain constant region of the anti-LAG-3 arm is a kappa constant region, and the light chain constant region of the anti-PD-1 arm is a lambda constant region.

The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction.

The polynucleotides of the present disclosure can be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present disclosure can readily be produced in mammalian cells, non-limiting examples of which includes CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed to purify proteins, including, but not limited to, antibodies, and such methods are known in the art.

In other embodiments of the present disclosure, cells, antibodies, or the nucleic acids encoding the same, are provided in isolated form. As used herein, the term "isolated" refers to a cell, protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

An antibody of the present disclosure, or a pharmaceutical composition comprising the same, may be administered by parenteral routes, non-limiting examples of which are subcutaneous administration and intravenous administration. An antibody of the present disclosure may be administered to a patient alone with pharmaceutically acceptable carriers, diluents, or excipients in single or multiple doses. Pharmaceutical compositions of the present disclosure can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

"Binds to human PD-1" as used herein in reference to the affinity of a human PD-1 agonist antibody for human PD-1 (SEQ ID NO: 39) or human PD-1 ECD, preferably, the human PD-1 ECD as shown in SEQ ID NO: 40, is intended to mean, unless indicated otherwise, a $K_D$ of about 1 $\chi 10^{-7}$ M. of about $1\times10^{-8}$ M, of about $1\times10^{-9}$ M, of about $5\times10^{-9}$ M, about $1\times10^{-10}$ M as determined by methods known in the art and/or by methods essentially as described herein, including, but not limited to, use of a surface plasmon resonance (SPR) biosensor at 25° C. or 37° C. More preferably, a human PD-1 agonist antibody of the present disclosure binds human PD-1 (i.e., SEQ ID NO: 39) or human PD-1 ECD (e.g., SEQ ID NO: 40), with a $K_D$ of between about $1\times10^{-8}$ M and about $5\times10^{-10}$ M as determined by methods known in the art and/or by methods essentially as described herein, including by use of a SPR biosensor at 25° C. or 37° C. Even more preferably, such an antibody will have an affinity for human PD-1 (i.e., SEQ ID NO: 39) or human PD-1 ECD (e.g., SEQ ID NO: 40), of between about $5\times10^{-8}$ M and about $5\times10^{-10}$ M as determined by methods known in the art and/or by methods essentially as described herein, including by use of a SPR biosensor at 25° C. or 37° C. Even more preferably, such an antibody will have Kon and Koff values for human PD-1 ECD (e.g., SEQ ID NO: 40) of about $1.0\times10^{-4}$ to about $1.0\times10^{-3}$ and about $1.3\times10^{5}$ to about $2.0\times10^{5}$, respectively (as determined by SPR using on BIAcore®8K essentially as described herein).

"Binds to human LAG-3" as used herein, in reference to the affinity of a human LAG-3 agonist antibody for human LAG-3 (SEQ ID NO: 41) or human LAG-3 ECD, preferably, the human LAG-3 ECD as shown in SEQ ID NO: 42, is intended to mean, unless indicated otherwise, a $K_D$ of about $1\times10^{-7}$ M, of about $1\times10^{-8}$ M, of about $1\times10^{-9}$ M, of about $5\times10^{-9}$ M, about $1\times10^{-10}$ M as determined by methods known in the art and/or by methods essentially as described herein, including, but not limited to, use of a surface plasmon resonance (SPR) biosensor at 25° C. or 37° C. More preferably, a human LAG-3 agonist antibody of the present disclosure binds human LAG-3 (i.e., SEQ ID NO: 41) or human LAG-3 (e.g., SEQ ID NO: 42), with a $K_D$ of between about $1\times10^{-8}$ M and about $5\times10^{-10}$ M as determined by methods known in the art and/or by methods essentially as described herein, including by use of a SPR biosensor at 25° C. or 37° C. Even more preferably, such an antibody will have an affinity for human LAG-3 (i.e., SEQ ID NO: 41) or human LAG-3 (e.g., SEQ ID NO: 42), of between about $5\times10^{-8}$ M and about $5\times10^{-10}$ M as determined by methods known in the art and/or by methods essentially as described herein, including by use of a SPR biosensor at 25° C. or 37° C. Even more preferably, such an antibody will have Kon and Koff values for human LAG-3ECD (e.g., SEQ ID NO: 40) of about $1.0\times10^{-4}$ to about $1.0\times10^{-3}$ and about $1.3\times10^{5}$ to about $2.0\times10^{5}$, respectively (as determined by SPR using on BIAcore®8K essentially as described herein).

Unless otherwise indicated herein, "LAG-3" refers to human LAG-3, and "PD-1" refers to human PD-1.

The term "binds" as used herein refers to the molecular interaction between two molecules, e.g., an antibody of the invention and LAG-3, PD-1, or both LAG-3 and PD-1. The term "bispecific binding" refers to binding to human LAG-3 and to human PD-1.

The terms "selectively binds" or "specifically binds" mean that an antibody of the invention interacts more frequently, more rapidly, with greater duration, with greater affinity, or with some combination of the above to human LAG-3, or to PD-1, or to both human LAG-3 and human PD-1, than do other substances. In one embodiment, "specifically binds" means that an antibody of the invention binds to human LAG-3, or to human PD-1, or to both human LAG-3 and human PD-1 with a $K_D$ of about 0.1 mM or less. In another embodiment, "specifically binds" means that an antibody of the invention binds to human LAG-3, or to human PD-1, or to both human LAG-3 and human PD-1 with a $K_D$ of about 0.01 mM or less. In another embodiment, "specifically binds" means that an antibody of the invention binds to human LAG-3, or to human PD-1, or to both human LAG-3 and human PD-1 with a $K_D$ of about 0.001 mM or less. In another embodiment, "specifically binds" means that an antibody of the invention binds to human LAG-3, or to human PD-1, or to both human LAG-3 and human PD-1 with a $K_D$ of about 0.0001 mM or less. In another embodiment, an antibody of the invention binds to human LAG-3 with a $K_D$ that is different than the $K_D$ with which the antibody binds to human PD-1. In another embodiment, an antibody binds to human LAG-3 about 10-fold more tightly than it binds to human PD-1.

In one embodiment, an antibody of the invention is an scFv molecule that binds to human LAG-3, or to human PD-1, or to both human LAG-3 and human PD-1. In another embodiment, the scFv molecule binds specifically to human LAG-3, or to human PD-1, or to both human LAG-3 and human PD-1.

The term "substantially pure" as used herein refers to material, e.g., an antibody of the invention, that is at least 50%, 60%, 70%, 80%, 90%, 95%, 96%, 97%, 98%, 99% or 100% free of contaminants.

Synonyms for "LAG-3" are LAG-3 and CD223.

As used herein the term "about" implies plus or minus ten percent of the stated value or range of values. For example: "about" 12, includes values ranging from 10.8 (inclusive) to 13.2 (inclusive); about 10 wt. percent encompasses formation that include between 9 (inclusive) to 11 (inclusive) wt. percent; and the like.

As used herein, the term "adaptive immunity" includes the arm of the immune response which, in contrast to the innate arm of the immune response is antigen specific and shows enhanced, secondary antigen-specific immune responses upon re-stimulation with the same antigen.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the invention or pharmaceutical composition comprising such an antibody that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. Such benefit includes any one or more of: an increased immune tolerance of transplanted organs: stabilized autoimmune disease or disorder: or improving signs or symptoms of an autoimmune disorder, etc. An effective amount can be readily determined by one skilled in the art, by the use of known techniques, and by observing results obtained under analogous circumstances. In determining the effective amount for a patient, a number of factors are considered by the attending diagnostician, including, but not limited to: the patient's size, age, and general health: the specific disease or disorder involved: the degree of, or involvement, or the severity of the disease or disorder: the response of the individual patient: the particular compound administered: the mode of administration: the bioavailability characteristics of the preparation administered: the dose regimen selected: the use of concomitant medication; and other relevant circumstances.

Dosage regimens for administering antibodies of the invention may be adjusted to provide the optimum desired response (e.g., a therapeutic effect).

As used herein, the term "effective response" of a patient or a patient's "responsiveness" to treatment refers to the clinical or therapeutic benefit imparted to a patient upon administration an antibody of the present disclosure. Such benefit includes any one or more of the following: an increased immune tolerance of transplanted organs: stabilized autoimmune disease or disorder: or improving signs or symptoms of an autoimmune disorder, etc.

A potential advantage of methods disclosed herein is the possibility of producing marked and/or prolonged relief in a patient suffering from an autoimmune disorder with an acceptable safety profile including acceptable tolerability, toxicities and/or adverse events, so that the patient benefits from the treatment method overall. The efficacy of the treatment of the present disclosure can be measured by various endpoints that are commonly used in evaluating treatments for various autoimmune disorders including, but not limited to, American College of Rheumatology (ACR) 20, ACR50, ACR70, Psoriasis Area and Severity Index (PASI) 50, PASI75, PASI90, PASI100, Systemic Lupus Erythmatosus Disease Activity Index (SLEDAI). Various other approaches to determining efficacy of any particular therapy of the present disclosure can be optionally employed, including, for example, immune cell activation markers, measures of inflammation, cell-cycle dependent biomarkers measurement visualization, and/or measurement of response through pain assessments.

The term "modified human IgG1" as used herein means a human IgG1 engineered to reduce the binding of the human IgG1 to at least one human Fc gamma receptor. Typically this is performed by mutating residues that lead to a reduction in the binding of the antibody to the Fc gamma receptor(s), e.g., P329A, L234A and L235 A mutations.

Methods for assaying LAG-3 activity in vitro are known to those of ordinary skill in the art, for example in Angin M, et al., *J. Immunol.* 2020: 204(4): 810-818.

Methods for assaying PD-1 activity in vitro are known to those of ordinary skill in the art, for example in Carpenito et al., *J Immunother Cancer* 2018: 6(1): 31.

In vivo murine models of immune activity are well known to those of ordinary skill in the art, as shown herein, and as disclosed, e.g., Vincelette J, et al., *Arthritis Res Ther.* 2007: 9(6): R123. doi: 10.1186/ar2331.

A DNA molecule of the present disclosure is a DNA molecule that comprises a non-naturally occurring polynucleotide sequence encoding a polypeptide having the amino acid sequence of at least one of the polypeptides in an antibody of the present disclosure.

The polynucleotides of the present disclosure may be expressed in a host cell after the sequences are operably linked to an expression control sequence. The expression vectors are typically replicable in the host organisms either as episomes or as an integral part of the host chromosomal DNA. Commonly, expression vectors contain selection markers, e.g., tetracycline, neomycin, and dihydrofolate reductase, to permit detection of those cells transformed with the desired DNA sequences.

An expression vector containing the polynucleotide sequences of interest (e.g., the polynucleotides encoding the polypeptides of an antibody of the invention and expression control sequences) can be transferred into a host cell by known methods, which vary depending on the type of host cells.

An antibody of the present disclosure may readily be produced in mammalian host cells, non-limiting examples of which includes CHO, NS0, HEK293 or COS cells. The host cells may be cultured using techniques known in the art.

Various methods of protein purification may be employed to purify an antibody of the present disclosure and such methods are known in the art and described, for example, in Deutscher, *Methods in Enzymology* 182: 83-89 (1990) and Scopes, *Protein Purification: Principles and Practice,* 3rd Edition, Springer, NY (1994).

Sequences referred to herein are numbered according to the sequence identifier numbers listed in Tables 1a and 1b. The sequences in Tables 1a and 1b are amino acid sequences, unless otherwise indicated.

TABLE 1a

Sequence identifier numbers.

| | Antibody A | | Antibody B | |
|---|---|---|---|---|
| | Anti-hLAG-3 Arm | Anti-hPD-1 Arm | Anti-hLAG-3 Arm | Anti-hPD-1 Arm |
| HCDR1 | 1 | 7 | 1 | 7 |
| HCDR2 | 2 | 8 | 2 | 8 |
| HCDR3 | 3 | 9 | 3 | 9 |
| LCDR1 | 4 | 10 | 4 | 10 |
| LCDR2 | 5 | 11 | 5 | 11 |
| LCDR3 | 6 | 12 | 6 | 12 |
| Variable Heavy (VH) | 13 | 17 | 13 | 17 |
| Variable Light (VL) | 14 | 18 | 14 | 18 |
| Constant Heavy (CH) | 15 | 19 | 29 | 30 |
| Constant Light (CL) | 16 | 20 | 16 | 20 |
| Heavy Chain (HC) | 21 | 23 | 31 | 32 |
| Light Chain (LC) | 22 | 24 | 22 | 24 |
| HC [DNA] | 25 | 27 | 33 | 34 |
| LC [DNA] | 26 | 28 | 26 | 28 |
| LAG-3_CH_X | 35 (wherein X is K or A) | | | |
| PD-1_CH_X | 36 (wherein X is K or A) | | | |
| LAG-3_HC_X | 37 (wherein X is K or A) | | | |
| PD-1_HC_X | 38 (wherein X is K or A) | | | |
| Human PD-1 | 39 | | | |
| Human PD-1 ECD-His | 40 | | | |
| Human LAG-3 | 41 | | | |
| Human LAG-3 ECD-His | 42 | | | |
| Cynomolgus LAG-3-ECD | 43 | | | |

TABLE 1b

Sequence identifier numbers.

| | Antibody C | | Antibody D | |
|---|---|---|---|---|
| | Anti-hLAG-3 Arm | Anti-hPD-1 Arm | Anti-hLAG-3 Arm | Anti-hPD-1 Arm |
| HCDR1 | 44 | 7 | 51 | 7 |
| HCDR2 | 45 | 46 | 52 | 46 |
| HCDR3 | 47 | 9 | 47 | 9 |
| LCDR1 | 48 | 10 | 48 | 10 |
| LCDR2 | 49 | 11 | 49 | 11 |
| LCDR3 | 50 | 12 | 50 | 12 |
| Variable Heavy (VH) | 53 | 55 | 54 | 55 |
| Variable Light (VL) | 56 | 57 | 56 | 57 |
| Constant Heavy (CH) | 58 | 59 | 58 | 59 |
| Constant Light (CL) | 60 | 20 | 60 | 20 |
| Heavy Chain (HC) | 61 | 63 | 62 | 63 |
| Light Chain (LC) | 64 | 65 | 64 | 65 |
| HC [DNA] | 66 | 68 | 67 | 68 |
| LC [DNA] | 69 | 70 | 69 | 70 |

SEQ ID NOS: 15 and 29 are identical, except that SEQ ID NO: 15 contains a lysine at amino acid residue position 205, and SEQ ID NO: 29 contains an alanine residue at position 205.

SEQ ID NOS: 19 and 30 are identical, except that SEQ ID NO: 19 contains a lysine at amino acid residue position 205, and SEQ ID NO: 30 contains an alanine residue at position 205.

SEQ ID NOS: 21 and 31 are identical, except that SEQ ID NO: 21 contains a lysine at amino acid residue position 328, and SEQ ID NO: 31 contains an alanine residue at position 328.

SEQ ID NOS: 23 and 32 are identical, except that SEQ ID NO: 23 contains a lysine at amino acid residue position 324, and SEQ ID NO: 32 contains an alanine residue at position 324.

SEQ ID NO: 35 (LAG-3_CH_X) is a consensus sequence, and contains an X residue at amino acid residue position 205, which corresponds to a lysine residue at position 205 in SEQ ID NO: 15, and to an alanine residue at position 205 in SEQ ID NO: 29, respectively.

SEQ ID NO: 36 (PD-1_CH_X) is a consensus sequence, and contains an X residue at amino acid residue position 205, which corresponds to a lysine residue at position 205 in SEQ ID NO: 29, and to an alanine residue at position 205 in SEQ ID NO: 30, respectively.

SEQ ID NO: 37 (LAG-3_HC_X) is a consensus sequence, and contains an X residue at amino acid residue position 328, which corresponds to a lysine residue at position 328 in SEQ ID NO: 21, and to an alanine residue at position 328 in SEQ ID NO: 31, respectively.

SEQ ID NO: 38 (PD-1_HC_X) is a consensus sequence, and contains an X residue at amino acid residue 324, which corresponds to a lysine residue at position 324 in SEQ ID NO: 23, and to an alanine residue at position 324 in SEQ ID NO: 32, respectively.

EXAMPLES

Antibody Expression and Purification

The human LAG-3 agonist antibodies of the invention and the human LAG-3/human PD-1 dual agonist bispecific antibodies of the present disclosure may be expressed and purified essentially as follows. An appropriate host cell, such as HEK 293 or CHO, may be either transiently or stably transfected with an expression system for secreting antibodies using an optimal predetermined heavy chain: light chain vector ratio or a single vector system encoding both heavy chain and light chain. The antibody or bispecific antibody of the present disclosure may be either transiently or stably transfected with an expression system for secreting antibodies using one or more DNA molecules encoding for a heavy chain and a light chain (for the human LAG-3 agonist antibody of the invention), or a first heavy chain, a first light chain, a second heavy chain and a second light chain (for the human LAG-3/human PD-1 dual agonist bispecific antibody of the present disclosure).

The antibodies may be purified using one of many commonly-used techniques. For example, the medium may be conveniently applied to a MabSelect column (GE Healthcare), or KappaSelect column (GE Healthcare), that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7.0 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The purified antibody may be concentrated and/or sterile filtered using common techniques. Soluble aggregate, multimers and mispairings may be effectively removed by common techniques, including size exclusion, hydrophobic interaction, ion exchange, multimodal, affinity or hydroxyapatite chromatography. The purified antibody may be immediately frozen at −70° C. or may be lyophilized.

Binding to Human LAG-3 and Human PD-1

A Biacore® T200 (Cytiva, Marlborough, MA) was used to measure the binding kinetics and affinities of the LAG-3 antibody to the LAG-3 soluble extracellular domain (ECD) and the bispecific antibody to soluble LAG-3-ECD and PD-1-ECD (human: Sino Biologicals, Cat #10377-H08H; cynomolgus: Sino Biologicals, Cat #90311-C08H) by surface plasmon resonance. Samples were diluted in HBS-EP+ (10 mM Hepes, 150 mM NaCl, 3 mM EDTA, 0.05% Tween-20, pH 7.6) (Teknova Cat #H8022) with 5 g/L of BSA (Jackson ImmunoResearch Cat #001-000-161) running buffer. PrismA Series S Sensor chip (Cat #29650263) is purchased from Cytiva.

Binding was evaluated using multi-cycle kinetics by an antibody capture method. Each cycle was performed at either 37° C. or 25° C. at a flow rate of 10 μL/min for antibody capture to the PrismA chip and 100 μL/min for analyte association (with 120 sec contact time) and dissociation (900 sec). Each cycle consisted of the following steps: injection of bispecific antibody at 1 μg/mL in HBS-EP+ targeting Rmax values of 125 RU (LAG-3 arm), 294 RU (PD-1 arm) and 63 RU (LAG-3 antibody) on flow cell, injection of analyte in HBS-EP+(concentration range of 62.5 nM to 0.25 nM by two-fold serial dilution for both human PD-1-ECD-His (SEQ ID NO: 40) and human LAG-3-His (SEQ ID NO: 42) followed by 900-second dissociation phase, and regeneration using 10 μL of 10 mM glycine hydrochloride, pH 1.5 over a 60-second contact time utilizing a 10 μL/min flow rate. All analyte concentrations were determined utilizing monomeric molecular weight (MW) values. Association rates ($k_{on}$) and dissociation rates ($k_{off}$) for LAG-3-ECD and PD-1-ECD were evaluated using double referencing by flow-cell one reference subtraction in addition to 0 nM blank subtraction and fit to "1:1 (Langmuir) binding" model in the BIAevaluation software version 4.1. The dissociation constant ($K_D$) was calculated from the binding kinetics according to the relationship $K_D=K_{off}/K_{on}$. Stoichiometry=$[RU_{max}/RU_{captured}]/[MW_{analyte}/MW_{antibody}]$ where $MW_{AntibodyA}$ is 150 kDa. Values are reported as mean±standard deviation.

In experiments performed essentially as described above, the results in Tables 2 and 3 were obtained. The results in Table 2a demonstrate that Antibody E bound to human and cynomolgus LAG-3-ECD. The results in Table 2b demonstrate that Antibody F bound to human LAG-3-ECD. The results in Table 2c demonstrate that Antibody G bound to human and no binding to cynomolgus LAG-3-ECD was detected at the concentration tested. The results in Table 3a show that Antibody A bound to human PD-1-ECD, human LAG-3-ECD, cynomolgus PD-1-ECD and cynomolgus LAG-3-ECD. The results in Table 3b show that Antibody B bound to human PD-1-ECD, human LAG-3-ECD, cynomolgus PD-1-ECD and cynomolgus LAG-3-ECD. The results in Table 3c show that Antibody C bound to human PD-1-ECD and human LAG-3-ECD. The results in Table 3d show that Antibody D bound to human PD-1-ECD and human LAG-3-ECD.

TABLE 2a

LAG-3 binding data for the human LAG-3 Antibody E.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 37° C. | Human LAG-3-ECD | 1.5E+08 | 1.6E−01 | 1.0E−09 |
| | Cynomolgus LAG-3-ECD | 1.1E+08 | 4.2E−03 | 3.8E−11 |

TABLE 2b

LAG-3 binding data for the human LAG-3 Antibody F.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 37° C. | Human LAG-3-ECD | 6.7E+05 | 1.9E−03 | 2.9E−09 |
| | Cynomolgus LAG-3-ECD | | N.B.[a] | |

[a]No binding observed up to 1000 nM.

TABLE 2c

LAG-3 binding data for the human LAG-3 Antibody G.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 37° C. | Human LAG-3-ECD | 6.4E+05 | 2.4E−03 | 3.7E−09 |
| | Cynomolgus LAG-3-ECD | | N.B.[a] | |

[a]No binding observed up to 1000 nM.

TABLE 3a

PD-1 and LAG-3 binding data for Antibody A.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 25° C. | Human PD-1-ECD | 7.5E−05 | 5.7E−04 | 7.6E−10 |
| | Cynomolgus PD-1-ECD | 1.3E+06 | 2.0E−03 | 1.6E−09 |
| | Human LAG-3-ECD | 3.4E+07 | 1.9E−02 | 5.5E−10 |
| | Cynomolgus LAG-3-ECD | 5.4E+07 | 1.7E−03 | 3.1E−11 |
| 37° C. | Human PD-1-ECD | 2.5E+06 | 1.7E−03 | 6.6E−10 |
| | Cynomolgus PD-1-ECD | 2.5E+06 | 8.7E−03 | 3.5E−09 |
| | Human LAG-3-ECD | SS[b] | | 5.7E−09 |
| | Cynomolgus LAG-3-ECD | 2.0E+07 | 1.0E−02 | 5.1E−10 |

[b]SS: Steady-state equilibrium model. Unable to fit kinetic parameters due to fast-on and fast-off rates.

TABLE 3b

PD-1 and LAG-3 binding data for Antibody B.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 25° C. | Human PD-1-ECD | 7.7E+05 | 5.8E−04 | 7.6E−10 |
| | Cynomolgus PD-1-ECD | 1.7E+06 | 1.8E−03 | 1.1E−09 |
| | Human LAG-3-ECD | 4.3E+07 | 2.3E−02 | 5.3E−10 |
| | Cynomolgus LAG-3-ECD | 5.5E+07 | 1.7E−03 | 3.1E−11 |
| | Human PD-1-ECD | 2.4E+06 | 1.5E−03 | 6.5E−10 |
| | Cynomolgus PD-1-ECD | 2.8E+06 | 8.8E−03 | 3.1E−09 |
| 37° C. | Human LAG-3-ECD | 5.5E+07 | 3.4E−01 | 6.1E−09 |
| | Cynomolgus LAG-3-ECD | 2.0E+07 | 9.8E−03 | 4.8E−10 |

TABLE 3c

Binding data for Antibody C.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 25° C. | Human PD-1-ECD | 7.5E+05 | 1.1E−03 | 1.4E−09 |
| | Human LAG-3-ECD | 4.7E+05 | 6.6E−04 | 1.4E−09 |
| 37° C. | Human PD-1-ECD | 2.6E+06 | 1.6E−03 | 6.1E−10 |
| | Human LAG-3-ECD | 1.4E+06 | 2.8E−03 | 2.0E−09 |

TABLE 3d

Binding data for Antibody D.

| | Species | On Rate $(k_{on})$ $(M^{-1}s^{-1})$ | Off Rate $(k_{off})$ $(s^{-1})$ | Affinity $(K_D)$ (M) |
|---|---|---|---|---|
| 25° C. | Human PD-1-ECD | 7.1E+05 | 6.3E−04 | 8.8E−10 |
| | Human LAG-3-ECD | 3.8E+05 | 7.4E−04 | 2.0E−09 |
| 37° C. | Human PD-1-ECD | 2.2E+06 | 1.8E−03 | 8.3E−10 |
| | Human LAG-3-ECD | 2.3E+06 | 2.8E−03 | 1.2E−09 |

Peripheral Mononuclear Cell Binding Assay

The ability of the human LAG-3/PD-1 dual agonist antibodies disclosed herein to bind to cell surface human or cynomolgus monkey LAG-3/PD-1 can be measured using a flow cytometry assay.

Briefly, human peripheral blood mononuclear cells (PBMCs) were isolated from healthy human Trima LRS (San Diego Blood Bank; San Diego, CA) using Ficoll (GE Healthcare #17144002), and activated with 0.5 ug/mL plate-bound anti-CD3 (Biolegend #300302) for 3 days in Complete RPMI (RPMI, Corning #MT10041CV; 10% FCS, Corning #MT35011CV; 1× Glutamax, Gibco #35050061; 1× P/S, Corning #30002CI; 1×BME, Gibco #21985023; 1× MEM, Gibco #11140050, 1× Sodium Pyruvate, Corning #25-000-CI) at 37° C. 5% CO2.

Cynomolgus PBMCs were isolated from whole blood (BioIVT #NHP01WBK2-0000861) using 90% Ficoll in PBS (Corning #21-031-CM), and activated with 2 ug/mL plate-bound anti-CD3 (BD #551916) for 3 days in the RPMI as described above.

Cells were incubated with 10-12 point, 3-fold serial dilutions of the respective labeled antibody (Invitrogen #S20026, Invitrogen #C20029), starting at 30 ug/mL, in PBS+2% FCS for 30 minutes at 4° C. and containing the following: CD4 eBioscience #12-0047-42 or Biolegend #344634; CD8 eBioscience #25-0088-42; CD3 eBioscience 56-0038-82 for human cells and BD #557917 for cyno cells; CD33 eBioscience 45-0338-42 for human cells; Live/Dead eBioscience #65-0865-18. After washing thoroughly, cells were processed on a BD Fortessa or Fortessa X20 cytometer, and data were analyzed with Flowjo software (BD Biosciences). Percent of cells bound by the respective antibody is quantified and graphed with Prism (Graphpad, San Diego, CA).

In experiments performed essentially as described above, the data in Table 4 were obtained. Antibody A and Antibody B bound cell membrane-expressed human LAG-3/PD-1 and cynomolgus LAG-3/PD-1, as shown in Table 4a (n=3). Antibody C and Antibody D bound cell membrane-expressed human LAG-3/PD-1 and cynomolgus LAG-3/PD-1, as shown in Table 4b (n=3). Antibody E and Antibody F bound cell membrane-expressed human LAG-3, as shown in Table 4c (n=3).

TABLE 4a

Peripheral Mononuclear Cell Binding by Bispecific Antibodies A and B.

| | Human | | Cyno | |
|---|---|---|---|---|
| Molecule | CD4 EC50 +/− SEM, (ng/mL) | CD8 EC50 +/− SEM, (ng/mL) | CD4 EC50 +/− SEM, (ng/mL) | CD8 EC50 +/− SEM, (ng/mL) |
| Antibody A | 35.7 +/− 7.2 | 6.8 +/− 0.8 | 29.3 +/− 7.4 | 16.7 +/− 3.5 |
| Antibody B | 42.3 +/− 10.9 | 7.7 +/− 0.5 | 33.7 +/− 8.4 | 18.0 +/− 2.9 |
| Isotype hG1 | — | — | — | — |

TABLE 4b

Peripheral Mononuclear Cell Binding by Bispecific Antibodies C and D.

| | Human | | Cyno | |
|---|---|---|---|---|
| Molecule | CD4 EC50 +/− SEM, (ng/mL) | CD8 EC50 +/− SEM, (ng/mL) | CD4 EC50 +/− SEM, (ng/mL) | CD8 EC50 +/− SEM, (ng/mL) |
| Antibody C | 95 +/− 4.0 | 110 +/− 5.8 | 54 +/− 14.7 | 103.3 +/− 17.6 |
| Antibody D | 52 +/− 1.7 | 48.7 +/− 3.4 | 25.7 +/− 6.6 | 35.7 +/− 6.9 |
| Isotype hG1 | — | — | — | — |

TABLE 4c

Peripheral Mononuclear Cell Binding by Antibodies E and F.

| | Human | | Cyno | |
|---|---|---|---|---|
| Molecule | CD4 EC50 +/− SEM, (ng/mL) | CD8 EC50 +/− SEM, (ng/mL) | CD4 EC50 +/− SEM, (ng/mL) | CD8 EC50 +/− SEM, (ng/mL) |
| Antibody E | 8.7 +/− 0.65 | 3.4 +/− 0.42 | 10.5 +/− 1.0 | 6.5 +/− 0.96 |
| Antibody F | 2233 +/− 66 | 883 +/− 109 | inactive | inactive |
| Isotype hG1 | — | — | — | — |

PD-1 and LAG-3 Dimerization Assay

The induction of dimerization of PD-1 and LAG-3 was measured in a cell-based enzyme fragment complementation assay in which bringing the two receptors together in close proximity induces a measurable luminescent signal in a dose-dependent manner.

For the assay, a PathHunter® U2OS PD-1/LAG-3 Dimerization Assay (Eurofins DiscoveRx) was utilized, which includes a cell line and assay components. The cell line was a U2OS cell line expressing the extracellular domain of human PD-1 (aa 1-199) fused to an EA (enzyme acceptor) subunit of beta-galactosidase and the extracellular domain of human LAG-3 (aa 1-477) fused to a PKI enzyme donor subunit of beta-galactosidase (Eurofins DiscoveRx #83-0009C3). Cells were maintained in supplemented Assay-Complete™ Cell Culture Kit-103 media (#92-3103G) with 250 μg/ml hygromycin B and 500 μg/ml G418.

After detaching with Cell Detachment Reagent (#92-0009), the cell line was seeded at 5,000 cells per well (in 80 μl Cell Plating 5 reagent (#93-0563R5A)), into 96-well white opaque plates (Costar #35-3296). Cells were incubated overnight at 37° C., 90% RH, 5% $CO_2$. The next day, compounds (at 5× the final concentrations) were serially diluted 1:5 in polypropylene plates in Protein Dilution Buffer (#92-0023M). Compounds were added to the cells in 20 μl, in triplicate wells per concentration. (The final concentration range of compounds was 0.00128-100 nM.) Cells were incubated for 30 minutes at 37° C., 90% RH, 5% $CO_2$. Plates were cooled to room temperature for 10 minutes, then 100 μl per well of Flash substrate/cell assay buffer mix (from PathHunter® Flash Detection Kit, #93-0247) was added. Plates were incubated undisturbed for 1 hour in the dark at room temperature. Plates were sealed with TopSeals (Perkin Elmer), then luminescence was read on a Biotek Synergy Neo2 multimode reader (0.1 second per well, PMT gain of 135).

EC50 values for induction of PD-1 and LAG-3 dimerization were calculated with GraphPad Prism 9, using Log-transformed X values. Nonlinear regression (curve fit) analysis (sigmoidal dose response, variable slope) may be performed on the log-transformed data to obtain EC50 values.

In experiments performed essentially as described in this assay, Antibody A dose dependently induced PD-1 and LAG-3 dimerization with an EC50 mean of 2.97 nM+/−1.14 (SE) (Table 5a), while Antibody B had an EC50 mean of 2.47 nM+/−1.26 (SE) (Table 5b). The combination of the human LAG-3 agonist arm plus the human PD-1 agonist arm did not induce PD-1 and LAG-3 dimerization in this assay.

The data in Table 5a also indicate that Antibody A and Antibody B bind to human PD-1 and human LAG-3 (and bring them into close proximity) in a cell based system.

The data in Table 5b also indicate that Antibody C and Antibody D bind to human PD-1 and human LAG-3 (and bring them into close proximity) in a cell based system.

Data shown in Tables 5a and 5b are relative luminescence units from one out of two experiments.

TABLE 5a

Dimerization assay data for Antibodies A and B.

| Concentration (nM) | Antibody A | Antibody B | Human LAG-3 agonist antibody arm + human PD-1 agonist antibody arm antibody combination |
|---|---|---|---|
| 100 | 74,923 | 74,621 | 21,249 |
| 20 | 78,434 | 78,462 | 23,560 |
| 4 | 63,289 | 70,592 | 19,246 |
| 0.8 | 35,743 | 42,296 | 22,769 |
| 0.16 | 27,799 | 31,074 | 21,165 |
| 0.032 | 22,385 | 26,080 | 20,535 |
| 0.0064 | 22,490 | 24,326 | 22,072 |
| 0.00128 | 22,123 | 23,391 | 23,152 |

TABLE 5b

Dimerization assay data for Antibodies C and D.

| Concentration (nM) | Antibody C | Antibody D | Human LAG-3 agonist antibody arm + human PD-1 agonist antibody arm antibody combination |
|---|---|---|---|
| 100 | 85,208 | 111,375 | 25,231 |
| 20 | 77,602 | 98,484 | 23,761 |
| 4 | 71,108 | 78,493 | 22,582 |
| 0.8 | 52,200 | 56,776 | 22,114 |
| 0.16 | 30,962 | 34,749 | 22,435 |
| 0.032 | 23,767 | 27,676 | 22,813 |
| 0.0064 | 20,234 | 22,830 | 22,122 |
| 0.00128 | 20,480 | 23,767 | 21,928 |

Inhibition of T-Cell Proliferation

The ability of the human LAG-3/human PD-1 dual agonist bispecific antibodies disclosed herein to inhibit T cell proliferation can be measured as follows.

Briefly, human peripheral blood mononuclear cells (PBMCs) were isolated from healthy human Trima LRS (San Diego Blood Bank; San Diego, CA) using Ficoll (GE Healthcare #17144002). Isolated PBMCs are labeled with a proliferation dye (eBioscience #65-0842-90) for 30 minutes room temp, then washed thoroughly.

Labeled PBMCs were treated with 10-12 point, 3-fold serial dilution of the respective antibodies starting at 30 ug/mL final in Complete RPMI (RPMI, Corning #MT10041CV; 10% FCS, Corning #MT35011CV; 1× Glutamax, Gibco #35050061; 1× P/S, Corning #30002CI; 1× BME, Gibco #21985023; 1×MEM, Gibco #11140050, 1× Sodium Pyruvate, Corning #25-000-CI) for 30 minutes room temp. Cells were then stimulated with 4 ng/ml SEB (Toxin Technologies BT2021M) final in Complete RPMI for 3 days at 37° ° C. with 5% $CO_2$. Cells were then washed thoroughly.

Cells were stained with the following for 30 minutes at 4° C.: non-competing PD-1, Biolegend 329904; CD4 eBioscience #12-0047-42 or Biolegend #344634; CD33, eBioscience #45-0338-42; CD8 eBioscience #25-0088-42; internal non-competing LAG-3 conjugated to Alexa 647, Invitrogen A20186; CD3 eBioscience 56-0038-82 and Live/Dead eBioscience #65-0865-18. After washing thoroughly, cells were processed on a BD Fortessa or Fortessa X20 cytometer, and data were analyzed with Flowjo software (BD Biosciences). Percent of cells proliferated was quantified and graphed with Prism (Graphpad, San Diego, CA).

In experiments performed essentially as described above, Antibodies A-D each inhibited human primary T cell proliferation, as shown in Tables 6a and 6b. Antibodies E and F also each inhibited primary T cell proliferation, as shown in Table 6c.

TABLE 6a

Inhibition of Human T cell Proliferation by Antibodies A and B.

| Molecule | CD4 IC50 +/− SEM (ng/mL) | CD8 IC50 +/− SEM (ng/mL) |
|---|---|---|
| Antibody A | 294 +/− 170 | 414 +/− 152 |
| Antibody B | 2218 +/− 789 | 1116 +/− 600 |
| Isotype hG1 | — | — |

TABLE 6b

Inhibition of Human T cell Proliferation by Antibodies C and D.

| Molecule | CD4 IC50 +/− SEM (ng/mL) | CD8 IC50 +/− SEM (ng/mL) |
|---|---|---|
| Antibody C | 1543 +/− 1419 | 743 +/− 524 |
| Antibody D | 2717 +/− 2202 | 533 +/− 357 |
| Isotype hG1 | — | — |

TABLE 6c

Inhibition of Human T cell Proliferation by Antibodies E and F.

| Molecule | CD4 IC50 +/− SEM (ng/mL) | CD8 IC50 +/− SEM (ng/mL) |
|---|---|---|
| Antibody E | 1567 +/− 1345 | 52 +/− 44 |
| Antibody F | 310 +/− 30 | 206 +/− 155 |
| Isotype hG1 | — | — |

Mouse Graft-Versus-Host Disease (GVHD) In Vivo Model

To demonstrate the immune modulatory activity of a PD-1/LAG-3 bispecific antibody of the invention, a humanized model of xenogeneic GvHD can be utilized. The model is generated by the engraftment of immunodeficient mice with human PBMCs. Human immune cells recognize the mouse as foreign and mount an immune response resulting in significant increases in human pro-inflammatory cytokines, immune cell activation, expansion and extravasation into tissues, ultimately resulting in weight loss and multi-system organ failure. Importantly, the inflammatory response is driven by human cells and thus human specific treatments can be interrogated in the model.

Briefly described, female NSG mice (NOD.Cg-Prkdescid Il2rgtm1Wjl/SzJ, JAX Labs, Stock #05557) are housed 3 per cage at 72° C. under a 12 hour light:dark cycle and allowed food and water ad libitum (n=76). Human PBMCs are isolated from an LRS tubes obtained from blood donor (San Diego Blood Bank) using SepMate 50 Ficoll preparation tubes according to the manufacturer's instructions (STEMCELL Technologies, Vancouver, BC). Freshly isolated PBMCs are suspended in PBS at $1.2\times10^8$ cells/mL and mice are engrafted with 100 μL PBMC suspension intravenously on day 0 ($1.2\times10^7$/mouse): 72 mice receive PBMCs and 4 mice remain non-engrafted controls.

On day 1 post engraftment, mice are divided into 9 weight matched (n-groups (n=8/group) and dosed subcutaneously with the bispecific antibody at 0.1, 1.0, or 3.0 mg/kg. Dosing continues weekly for the remainder of the experiment. Health checks and body weight measurements are performed routinely. Mice that lose 20% of their starting weight or are in obvious distress are euthanized. Clinical signs common to this model are scruffy hair, hunched body, wasting, and labored breathing or movement.

When the majority of isotype control mice are in need of euthanasia due to the progression of disease, all mice are sacrificed. For all sacrificed mice, blood is collected by cardiac puncture under isoflurane anesthesia into EDTA tubes: additionally, an interim blood sample on Day 10 is obtained by retro-orbital sinus. Blood from both collections is clarified by centrifugation for human plasma cytokine analysis. Body weight change is calculated as a percentage of their baseline weight: (Day (x) weight/Day 0 weight) *100. Mice requiring euthanasia prior to the end of the study have the last body weight measurement permutated to the end. Plasma cytokines are measured using the Mesoscale Discovery Human Th1/Th2 10-Vplex (Rockville, Maryland) according to the manufacturer's instructions. Data are graphed and statistics are calculated using Prism Software (GraphPad, San Diego, CA). Differences in weights between groups are determined by 2-way RM-ANOVA with Tukey's post hoc test. Differences in plasma cytokine levels are determined by 1-way ANOVA with Tukey's post hoc test. Differences between test groups are considered significant if $p<0.05$.

Engraftment of human PBMCs from elicited GvHD, as evidenced by marked wasting in NSG mice, which required study termination on Day 36 post engraftment. Treatments with a human LAG-3/human PD-1 dual agonist bispecific antibody can significantly attenuate disease progression, as measured by a reduction in weight loss in mice in a dose dependent manner. Additionally, a human LAG-3/human PD-1 dual agonist bispecific antibody can inhibit the pronounced increase in plasma human pro-inflammatory cytokines associated with disease progression. Therefore, a human LAG-3/human PD-1 dual agonist bispecific antibody can attenuate the human immune cell pathogenicity, and can reduce disease progression in a humanized GvHD model.

| Amino Acid and Nucleotide Sequences |
|---|
| SEQ ID NO: 1<br>(LAG-3 HCDR1 amino acid sequence)<br>KASGYTFTGYYMH |
| SEQ ID NO: 2<br>(LAG-3 HCDR2 amino acid sequence)<br>WINPNSGDTNYAQKFQG |
| SEQ ID NO: 3<br>(LAG-3 HCDR3 amino acid sequence)<br>AREGDSSGWHGGWFDP |
| SEQ ID NO: 4<br>(LAG-3 LCDR1 amino acid sequence)<br>RSSQSLLDSAEGSTYLD |
| SEQ ID NO: 5<br>(LAG-3 LCDR2 amino acid sequence)<br>YTLSYRAS |
| SEQ ID NO: 6<br>(LAG-3 LCDR3 amino acid sequence)<br>MQRVEFPYT |
| SEQ ID NO: 7<br>(PD-1 HCDR1 amino acid sequence)<br>KVSGYSLSKYDMS |
| SEQ ID NO: 8<br>(PD-1 HCDR2 amino acid sequence)<br>IIYTSGYTDYAQEFQG |
| SEQ ID NO: 9<br>(PD-1 HCDR3 amino acid sequence)<br>ATGNPYYTNGFNS |
| SEQ ID NO: 10<br>(PD-1 LCDR1 amino acid sequence)<br>QASQSPNNLLA |
| SEQ ID NO: 11<br>(PD-1 LCDR2 amino acid sequence)<br>YGASDLPS |
| SEQ ID NO: 12<br>(PD-1 LCDR3 amino acid sequence)<br>QNNYYVGPVSYA |
| SEQ ID NO: 13<br>(LAG-3 Variable Heavy amino acid sequence)<br>QVQLVQSGAEVKKPGASVKVSCKASGYTFTGYYMHWVRYAPGQGLEWMGWINPNSG<br>DTNYAQKFQGRVTMTRDTSISTAYMELSRLRSDDTAVYYCAREGDSSGWHGGWFDPW<br>GRGTLVTVSS |

-continued

| Amino Acid and Nucleotide Sequences |
| --- |

SEQ ID NO: 14
(LAG-3 Variable Light amino acid sequence)
DIVMTQTPLSLPVTPGEPASISCRSSQSLLDSAEGSTYLDWFLRKPGDSPQLLIYTLSYRAS
GVPDRFSGSGSGTDFTLKISRVEAEDVGVYYCMQRVEFPYTFGQGTKVEIK SEQ ID NO: 15
(LAG-3 Constant Heavy amino acid sequence)
ASTKGPSVFPLAPCSKSTSGGTAALGCLVKDYFPEPVTVSWNSGALTSGVHTFPAVLQSS
GLYSLSSVVTVPSSSLGTQTYICNVNHKPSNTKVDKRVEPDSGDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPRRPRVYTLPPSR
EEMTKNQVSLVCLVKGFYPSDIAVEWESNGQPENNYKTTPPVLDSDGSFFLYSVLTVDK
SRWQQGNVFSCSVMHEALHNHYTQKSLSLSPGK SEQ ID NO: 16
(LAG-3 Constant Light amino acid sequence)
RTVAAPSVFIFPPSKEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ ID NO: 17
(PD-1 Variable Heavy amino acid sequence)
QVQLVQSGAEVKKPGASVKVSCKVSGYSLSKYDMSWVRKAPGKGLEWMGIIYTSGYT
DYAQEFQGRVTMTEDTSTDTAYMELSSLRSEDTAVYYCATGNPYYTNGFNSWGQGTL
VTVSS SEQ ID NO: 18
(PD-1 Variable Light amino acid sequence)
RIQMTQSPSSLSASVGDRVTITCQASQSPNNLLAWYQDKPGKAPKLLIYGASDLPSGVPS
RFSGSGSGTDFTLTISSLQPEDFATYYCQNNYYVGPVSYAFGGGTKVEIK SEQ ID NO: 19
(PD-1 Constant Heavy amino acid sequence)
ASTKGPSVFPLAPSSKSTSGGTAALGCLVKDYFPEPVTVSWNSGALTSGVATGPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTDNQVSLTCLVKGFYPSDIAVEWESNGQPENNYKTTPPVLMSDGSFFLASKLTVDK
SRWQQGNVFSCSVMHEALHNHYTQKSLSLSPGK SEQ ID NO: 20
(PD-1 Constant Light amino acid sequence)
GQPKAAPSVTLFPPSSEELQANKATLVCYISDFYPGAVTVAWKADSSPVKAGVETTTPSK
QSNNKYAAWSYLSLTPEQWKSHRSYSCQVTHEGSTVEKTVAPTEC SEQ ID NO: 21
(LAG-3 Heavy Chain amino acid sequence)
QVQLVQSGAEVKKPGASVKVSCKASGYTFTGYYMHWVRYAPGQGLEWMGWINPNSG
DTNYAQKFQGRVTMTRDTSISTAYMELSRLRSDDTAVYYCAREGDSSGWHGGWFDPW
GRGTLVTVSSASTKGPSVFPLAPCSKSTSGGTAALGCLVKDYFPEPVTVSWNSGALTSGV
HTFPAVLQSSGLYSLSSVVTVPSSSLGTQTYICNVNHKPSNTKVDKRVEPDSGDKTHTCP
PCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPRR
PRVYTLPPSREEMTKNQVSLVCLVKGFYPSDIAVEWESNGQPENNYKTTPPVLDSDGSFF
LYSVLTVDKSRWQQGNVFSCSVMHEALHNHYTQKSLSLSPGK SEQ ID NO: 22
(LAG-3 Light Chain amino acid)
DIVMTQTPLSLPVTPGEPASISCRSSQSLLDSAEGSTYLDWFLRKPGDSPQLLIYTLSYRAS
GVPDRFSGSGSGTDFTLKISRVEAEDVGVYYCMQRVEFPYTFGQGTKVEIKRTVAAPSV
FIFPPSKEQLKSGTASVVCLLNNFYPREAKVQWKVDNALQSGNSQESVTEQDSKDSTYS
LSSTLTLSKADYEKHKVYACEVTHQGLSSPVTKSFNRGEC SEQ ID NO: 23
(PD-1 Heavy Chain amino acid sequence)
QVQLVQSGAEVKKPGASVKVSCKVSGYSLSKYDMSWVRKAPGKGLEWMGIIYTSGYT
DYAQEFQGRVTMTEDTSTDTAYMELSSLRSEDTAVYYCATGNPYYTNGFNSWGQGTL
VTVSSASTKGPSVFPLAPSSKSTSGGTAALGCLVKDYFPEPVTVSWNSGALTSGVATGPA
VLQSSGLYSLSSVVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYT
LPPSREEMTDNQVSLTCLVKGFYPSDIAVEWESNGQPENNYKTTPPVLMSDGSFFLASKL
TVDKSRWQQGNVFSCSVMHEALHNHYTQKSLSLSPGK SEQ ID NO: 24
(PD-1 Light Chain amino acid sequence)
RIQMTQSPSSLSASVGDRVTITCQASQSPNNLLAWYQDKPGKAPKLLIYGASDLPSGVPS
RFSGSGSGTDFTLTISSLQPEDFATYYCQNNYYVGPVSYAFGGGTKVEIKGQPKAAPSVT -continued

| Amino Acid and Nucleotide Sequences |
|---|
| LFPPSSEELQANKATLVCYISDFYPGAVTVAWKADSSPVKAGVETTTPSKQSNNKYAAW<br>SYLSLTPEQWKSHRSYSCQVTHEGSTVEKTVAPTEC |
| SEQ ID NO: 25<br>(LAG-3 Heavy Chain DNA sequence)<br>CAGGTGCAGCTGGTGCAGTCTGGGGCTGAGGTGAAGAAGCCTGGGGCCTCAGTGAA<br>GGTCTCCTGCAAGGCTTCTGGATACACCTTCACCGGCTACTATATGCACTGGGTGCG<br>ATACGCCCCTGGACAAGGGCTTGAGTGGATGGGATGGATCAACCCTAACAGTGGTG<br>ACACAAACTATGCACAGAAGTTTCAGGGCAGGGTCACCATGACCAGGGACACGTCC<br>ATCAGCACAGCCTACATGGAGCTGAGCAGGCTGAGATCTGACGACACGGCCGTGTA<br>TTACTGTGCGAGAGAAGGGGACTCATCAGGATGGCACGGAGGGTGGTTCGACCCCT<br>GGGGAAGAGGAACACTGGTGACGGTGAGCTCGGCTAGCACCAAGGGCCCATCGGTC<br>TTCCCCCTGGCACCCTGCTCCAAGAGCACCTCTGGGGGCACAGCGGCCCTGGGCTGC<br>CTGGTCAAGGACTACTTCCCCGAACCGGTGACGGTGTCGTGGAACTCAGGCGCCCTG<br>ACCAGCGGCGTGCACACCTTCCCGGCTGTCCTACAGTCCTCAGGACTCTACTCCCTC<br>AGCAGCGTGGTGACCGTGCCCTCCAGCAGCTTGGGCACCCAGACCTACATCTGCAAC<br>GTGAATCACAAGCCCAGCAACACCAAGGTGGACAAGAGAGTTGAGCCCGACTCTGG<br>CGACAAAACTCACACATGCCCACCGTGCCCAGCACCTGAACTCCTGGGGGGACCGTC<br>AGTCTTCCTCTTCCCCCCAAAACCCAAGGACACCCTCATGATCTCCCGGACCCCTGA<br>GGTCACATGCGTGGTGGTGGACGTGAGCCACGAAGACCCTGAGGTCAAGTTCAACT<br>GGTATGTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAAGACTGGCTG<br>AATGGCAAGGAGTACAAGTGCAAGGTCTCCAACAAAGCCCTCCCAGCCCCCATCGA<br>GAAAACCATCTCCAAAGCCAAAGGGCAGCCCCGAAGACCACGGGTGTACACCCTGC<br>CCCCATCCCGGGAGGAGATGACCAAGAACCAAGTCAGCCTGGTCTGCCTGGTCAAA<br>GGCTTCTATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCCTCTATTCC<br>GTGCTCACCGTGGACAAGAGCAGGTGGCAGCAGGGGAACGTCTTCTCATGCTCCGTG<br>ATGCATGAGGCTCTGCACAACCACTACACGCAGAAGAGCCTCTCCCTGTCTCCGGGC<br>AAA |
| SEQ ID NO: 26<br>(LAG-3 Light Chain DNA sequence)<br>GATATTGTGATGACCCAGACTCCACTCTCCCTGCCCGTCACCCCTGGAGAGCCGGCC<br>TCCATCTCCTGCAGGTCTAGTCAGAGCCTCTTGGATAGTGCTGAAGGAAGCACCTAT<br>TTGGACTGGTTCCTGAGAAAGCCAGGGGACTCTCCACAGCTCCTGATCTATACGCTT<br>TCCTACCGGGCCTCTGGAGTCCCAGACAGGTTCAGTGGCAGTGGGTCAGGCACTGAT<br>TTCACACTGAAAATCAGCAGGGTGGAGGCTGAGGATGTTGGAGTTTATTACTGCATG<br>CAGAGGGTAGAATTTCCGTACACATTCGGACAGGGAACAAAGGTGGAAATCAAGCG<br>GACCGTGGCTGCACCATCTGTCTTCATCTTCCCGCCATCTAAGGAGCAGTTGAAATCT<br>GGAACTGCCTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTGTCACAGA<br>GCAGGACAGCAAGGACAGCACCTACAGCCTCAGCAGCACCCTGACGCTGAGCAAAG<br>CAGACTACGAGAAACACAAAGTCTACGCCTGCGAAGTCACCCATCAGGGCCTGAGC<br>TCGCCCGTCACAAAGAGCTTCAACAGGGGAGAGTGC |
| SEQ ID NO: 27<br>(PD-1 Heavy Chain DNA sequence)<br>CAAGTGCAGTTGGTGCAGTCGGGGGCAGAAGTGAAAAAGCCCGGCGCTTCGGTGAA<br>AGTGTCCTGCAAAGTGTCCGGCTATTCTTTGAGCAAATACGACATGTCATGGGTCAG<br>AAAGGCTCCCGGAAAGGGTCTGGAGTGGATGGGGATTATCTATACATCCGGCTACA<br>CCGATTACGCCCAAGAGTTCCAGGGGAGAGTCACCATGACTGAGGATACGTCCACC<br>GACACCGCCTACATGGAACTGTCCAGCCTGCGGTCCGAGGACACTGCGGTGTACTAC<br>TGCGCGACCGGAAACCCATACTACACCAATGGATTCAATAGCTGGGGACAGGGTAC<br>TCTTGTGACGGTGTCCAGCGCTAGCACCAAGGGCCCATCGGTCTTCCCCCTGGCACC<br>CTCCTCCAAGAGCACCTCTGGGGGCACAGCGGCCCTGGGCTGCCTGGTCAAGGACTA<br>CTTCCCCGAACCGGTGACGGTGTCGTGGAACTCAGGCGCCCTGACCAGCGGCGTGGC<br>CACCGGCCCGGCTGTCCTACAGTCCTCAGGACTCTACTCCCTCAGCAGCGTGGTGAC<br>CGTGCCCTCCAGCAGCTTGGGCACCCAGACCTACATCTGCAACGTGAATCACAAGCC<br>CAGCAACACCAAGGTGGACAAGAGAGTTGAGCCCAAATCTTGTGACAAAACTCACA<br>CATGCCCACCGTGCCCAGCACCTGAACTCCTGGGGGGACCGTCAGTCTTCCTCTTCC<br>CCCCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTATGTGGACGGC<br>GTGGAGGTGCATAATGCCAAGACAAAGCCGCGGGAGGAGCAGTACAACAGCACGTA<br>CCGTGTGGTCAGCGTCCTCACCGTCCTGCACCAAGACTGGCTGAATGGCAAGGAGTA<br>CAAGTGCAAGGTCTCCAACAAAGCCCTCCCAGCCCCCATCGAGAAAACCATCTCCAA<br>AGCCAAAGGGCAGCCCCGAGAACCACAGGTGTACACCCTGCCCCCATCCCGGGAGG<br>AGATGACCGACAACCAAGTCAGCCTGACCTGCCTGGTCAAAGGCTTCTATCCCAGCG<br>ACATCGCCGTGGAGTGGGAGAGCAATGGGCAGCCGGAGAACAACTACAAGACCACG<br>CCTCCCGTGCTGATGTCCGACGGCTCCTTCTTCCTCGCCTCCAAGCTCACCGTGGACA<br>AGAGCAGGTGGCAGCAGGGGAACGTCTTCTCATGCTCCGTGATGCATGAGGCTCTGC<br>ACAACCACTACACGCAGAAGAGCCTCTCCCTGTCTCCGGGCAAA |
| SEQ ID NO: 28<br>(PD-1 Light Chain DNA sequence)<br>AGAATCCAGATGACCCAGTCTCCATCCTCCCTGTCTGCATCTGTGGGAGACAGAGTC<br>ACCATCACTTGCCAGGCCAGTCAGAGCCCTAATAACCTCCTGGCCTGGTATCAGGAC |

Amino Acid and Nucleotide Sequences

AAACCAGGGAAAGCCCCTAAGCTCCTGATCTATGGTGCATCCGATCTGCCATCTGGG
GTCCCATCAAGGTTCAGTGGCAGTGGATCTGGGACAGATTTCACTCTCACCATCAGC
AGTCTGCAACCTGAAGATTTTGCAACTTACTACTGTCAGAACAATTATTATGTGGGA
CCAGTGAGCTATGCTTTCGGCGGAGGGACCAAGGTGGAGATCAAGGGCCAGCCTAA
AGCTGCCCCTAGCGTTACCCTTTTCCCACCGAGCTCCGAGGAGCTGCAGGCCAATAA
AGCAACCTTGGTCTGCTACATATCAGATTTTTACCCTGGCGCCGTGACCGTAGCATG
GAAAGCTGATTCATCCCCTGTGAAGGCCGGTGTTGAAACTACAACCCCTTCCAAACA
ATCTAACAATAAATACGCGGCATGGTCCTACCTGTCCTTGACACCCGAGCAGTGGAA
ATCTCACAGATCTTACAGCTGCCAGGTCACCCACGAGGGGAGCACTGTGGAGAAGA
CCGTCGCGCCCACTGAGTGC

SEQ ID NO: 29
(LAG-3 Constant Heavy amino acid sequence of Antibody B)
ASTKGPSVFPLAPCSKSTSGGTAALGCLVKDYFPEPVTVSWNSGALTSGVHTFPAVLQSS
GLYSLSSVVTVPSSSLGTQTYICNVNHKPSNTKVDKRVEPDSGDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCAVSNKALPAPIEKTISKAKGQPRRPRVYTLPPSR
EEMTKNQVSLVCLVKGFYPSDIAVEWESNGQPENNYKTTPPVLDSDGSFFLYSVLTVDK
SRWQQGNVFSCSVMHEALHNHYTQKSLSLSPGK SEQ ID NO: 30
(PD-1 Constant Heavy amino acid sequence of Antibody B)
ASTKGPSVFPLAPSSKSTSGGTAALGCLVKDYFPEPVTVSWNSGALTSGVATGPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCAVSNKALPAPIEKTISKAKGQPREPQVYTLPPSR
EEMTDNQVSLTCLVKGFYPSDIAVEWESNGQPENNYKTTPPVLMSDGSFFLASKLTVDK
SRWQQGNVFSCSVMHEALHNHYTQKSLSLSPGK SEQ ID NO: 31
(LAG-3 Heavy Chain amino acid sequence of Antibody B)
QVQLVQSGAEVKKPGASVKVSCKASGYTFTGYYMHWVRYAPGQGLEWMGWINPNSG
DTNYAQKFQGRVTMTRDTSISTAYMELSRLRSDDTAVYYCAREGDSSGWHGGWFDPW
GRGTLVTVSSASTKGPSVFPLAPCSKSTSGGTAALGCLVKDYFPEPVTVSWNSGALTSGV
HTFPAVLQSSGLYSLSSVVTVPSSSLGTQTYICNVNHKPSNTKVDKRVEPDSGDKTHTCP
PCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCAVSNKALPAPIEKTISKAKGQPRR
PRVYTLPPSREEMTKNQVSLVCLVKGFYPSDIAVEWESNGQPENNYKTTPPVLDSDGSFF
LYSVLTVDKSRWQQGNVFSCSVMHEALHNHYTQKSLSLSPGK SEQ ID NO: 32
(PD-1 Heavy Chain amino acid sequence of Antibody B)
QVQLVQSGAEVKKPGASVKVSCKVSGYSLSKYDMSWVRKAPGKGLEWMGIIYTSGYT
DYAQEFQGRVTMTEDTSTDTAYMELSSLRSEDTAVYYCATGNPYYTNGFNSWGQGTL
VTVSSASTKGPSVFPLAPSSKSTSGGTAALGCLVKDYFPEPVTVSWNSGALTSGVATGPA
VLQSSGLYSLSSVVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCAVSNKALPAPIEKTISKAKGQPREPQVYT
LPPSREEMTDNQVSLTCLVKGFYPSDIAVEWESNGQPENNYKTTPPVLMSDGSFFLASKL
TVDKSRWQQGNVFSCSVMHEALHNHYTQKSLSLSPGK SEQ ID NO: 33
(LAG-3 Heavy Chain DNA sequence of Antibody B)
CAGGTGCAGCTGGTGCAGTCTGGGGCTGAGGTGAAGAAGCCTGGGGCCTCAGTGAA
GGTCTCCTGCAAGGCTTCTGGATACACCTTCACCGGCTACTATATGCACTGGGTGCG
ATACGCCCCTGGACAAGGGCTTGAGTGGATGGGATGGATCAACCCTAACAGTGGTG
ACACAAACTATGCACAGAAGTTTCAGGGCAGGGTCACCATGACCAGGGACACGTCC
ATCAGCACAGCCTACATGGAGCTGAGCAGGCTGAGATCTGACGACACGGCCGTGTA
TTACTGTGCGAGAGAAGGGGACTCATCAGGATGGCACGGAGGGTGGTTCGACCCCT
GGGGAAGAGGAACACTGGTGACGGTGAGCTCGGCTAGCACCAAGGGCCCATCGGTC
TTCCCCCTGGCACCCTGCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAAC
GTGAATCACAAGCCCAGCAACACCAAGGTGGACAAGAGAGTTGAGCCCGACTCTGG
CGACAAAACTCACACATGCCCACCGTGCCCAGCACCTGAACTCCTGGGGGGACCGTC
AGTCTTCCTCTTCCCCCCAAAACCCAAGGACACCCTCATGATCTCCCGGACCCCTGA
GGTCACATGCGTGGTGGTGGACGTGAGCCACGAAGACCCTGAGGTCAAGTTCAACT
GGTATGTGGACGGCGTGGAGGTGCATAATGCCAAGACAAAGCCGCGGGAGGAGCAG
TACAACAGCACGTACCGTGTGGTCAGCGTCCTCACCGTCCTGCACCAAGACTGGCTG
AATGGCAAGGAGTACAAGTGCGCCGTCTCCAACAAAGCCCTCCCAGCCCCCATCGA
GAAAACCATCTCCAAAGCCAAAGGGCAGCCCCGAGACCACGGGTGTACACCCTGC -continued

| Amino Acid and Nucleotide Sequences |
| --- |
| CCCCATCCCGGGAGGAGATGACCAAGAACCAAGTCAGCCTGGTCTGCCTGGTCAAA<br>GGCTTCTATCCCAGCGACATCGCCGTGGAGTGGGAGAGCAATGGGCAGCCGGAGAA<br>CAACTACAAGACCACGCCTCCCGTGCTGGACTCCGACGGCTCCTTCTTCCTCTATTCC<br>GTGCTCACCGTGGACAAGAGCAGGTGGCAGCAGGGGAACGTCTTCTCATGCTCCGTG<br>ATGCATGAGGCTCTGCACAACCACTACACGCAGAAGAGCCTCTCCCTGTCTCCGGGC<br>AAA |
| SEQ ID NO: 34<br>(PD-1 Heavy Chain DNA sequence of Antibody B)<br>CAAGTGCAGTTGGTGCAGTCGGGGGCAGAAGTGAAAAAGCCCGGCGCTTCGGTGAA<br>AGTGTCCTGCAAAGTGTCCGGCTATTCTTTGAGCAAATACGACATGTCATGGGTCAG<br>AAAGGCTCCCGGAAAGGGTCTGGAGTGGATGGGGATTATCTATACATCCGGCTACA<br>CCGATTACGCCCAAGAGTTCCAGGGGAGAGTCACCATGACTGAGGATACGTCCACC<br>GACACCGCCTACATGGAACTGTCCAGCCTGCGGTCCGAGGACACTGCGGTGTACTAC<br>TGCGCGACCGGAAACCCATACTACACCAATGGATTCAATAGCTGGGGACAGGGTAC<br>TCTTGTGACGGTGTCCAGCGCTAGCACCAAGGGCCCATCGGTCTTCCCCCTGGCACC<br>CTCCTCCAAGAGCACCTCTGGGGGCACAGCGGCCCTGGGCTGCCTGGTCAAGGACTA<br>CTTCCCCGAACCGGTGACGGTGTCGTGGAACTCAGGCGCCCTGACCAGCGGCGTGGC<br>CACCGGCCCGGCTGTCCTACAGTCCTCAGGACTCTACTCCCTCAGCAGCGTGGTGAC<br>CGTGCCCTCCAGCAGCTTGGGCACCCAGACCTACATCTGCAACGTGAATCACAAGCC<br>CAGCAACACCAAGGTGGACAAGAGAGTTGAGCCCAAATCTTGTGACAAAACTCACA<br>CATGCCCACCGTGCCCAGCACCTGAACTCCTGGGGGGACCGTCAGTCTTCCTCTTCC<br>CCCCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTATGTGGACGGC<br>GTGGAGGTGCATAATGCCAAGACAAAGCCGCGGGAGGAGCAGTACAACAGCACGTA<br>CCGTGTGGTCAGCGTCCTCACCGTCCTGCACCAAGACTGGCTGAATGGCAAGGAGTA<br>CAAGTGCGCCGTCTCCAACAAAGCCCTCCCAGCCCCCATCGAGAAAACCATCTCCAA<br>AGCCAAAGGGCAGCCCCGAGAACCACAGGTGTACACCCTGCCCCCATCCCGGGAGG<br>AGATGACCGACAACCAAGTCAGCCTGACCTGCCTGGTCAAAGGCTTCTATCCCAGCG<br>ACATCGCCGTGGAGTGGGAGAGCAATGGGCAGCCGGAGAACAACTACAAGACCACG<br>CCTCCCGTGCTGATGTCCGACGGCTCCTTCTTCCTCGCCTCCAAGCTCACCGTGGACA<br>AGAGCAGGTGGCAGCAGGGGAACGTCTTCTCATGCTCCGTGATGCATGAGGCTCTGC<br>ACAACCACTACACGCAGAAGAGCCTCTCCCTGTCTCCGGGCAAA |
| SEQ ID NO: 35<br>(LAG-3_CH_X amino acid sequence)<br>ASTKGPSVFPLAPCSKSTSGGTAALGCLVKDYFPEPVTVSWNSGALTSGVHTFPAVLQSS<br>GLYSLSSVVTVPSSSLGTQTYICNVNHKPSNTKVDKRVEPDSGDKTHTCPPCPAPELLGG<br>PSVFLFPPKPKDTLMISRTPEVTCVVVDVSHEDPEVKFNWYVDGVEVHNAKTKPREEQY<br>NSTYRVVSVLTVLHQDWLNGKEYKCXVSNKALPAPIEKTISKAKGQPRRPRVYTLPPSR<br>EEMTKNQVSLVCLVKGFYPSDIAVEWESNGQPENNYKTTPPVLDSDGSFFLYSVLTVDK<br>SRWQQGNVFSCSVMHEALHNHYTQKSLSLSPGK (wherein X is K or A) |
| SEQ ID NO: 36<br>(PD-1 CH_X amino acid sequence)<br>ASTKGPSVFPLAPSSKSTSGGTAALGCLVKDYFPEPVTVSWNSGALTSGVATGPAVLQSS<br>GLYSLSSVVTVPSSSLGTQTYICNVNHKPSNTKVDKRVEPKSCDKTHTCPPCPAPELLGG<br>PSVFLFPPKPKDTLMISRTPEVTCVVVDVSHEDPEVKFNWYVDGVEVHNAKTKPREEQY<br>NSTYRVVSVLTVLHQDWLNGKEYKCXVSNKALPAPIEKTISKAKGQPREPQVYTLPPSR<br>EEMTDNQVSLTCLVKGFYPSDIAVEWESNGQPENNYKTTPPVLMSDGSFFLASKLTVDK<br>SRWQQGNVFSCSVMHEALHNHYTQKSLSLSPGK (wherein X is K or A) |
| SEQ ID NO: 37<br>(LAG-3_HC X amino acid sequence)<br>QVQLVQSGAEVKKPGASVKVSCKASGYTFTGYYMHWVRYAPGQGLEWMGWINPNSG<br>DTNYAQKFQGRVTMTRDTSISTAYMELSRLRSDDTAVYYCAREGDSSGWHGGWFDPW<br>GRGTLVTVSSASTKGPSVFPLAPCSKSTSGGTAALGCLVKDYFPEPVTVSWNSGALTSGV<br>HTFPAVLQSSGLYSLSSVVTVPSSSLGTQTYICNVNHKPSNTKVDKRVEPDSGDKTHTCP<br>PCPAPELLGGPSVFLFPPKPKDTLMISRTPEVTCVVVDVSHEDPEVKFNWYVDGVEVHN<br>AKTKPREEQYNSTYRVVSVLTVLHQDWLNGKEYKCXVSNKALPAPIEKTISKAKGQPRR<br>PRVYTLPPSREEMTKNQVSLVCLVKGFYPSDIAVEWESNGQPENNYKTTPPVLDSDGSFF<br>LYSVLTVDKSRWQQGNVFSCSVMHEALHNHYTQKSLSLSPGK (wherein X is K or A) |
| SEQ ID NO: 38<br>(PD-1 HC_X amino acid sequence)<br>QVQLVQSGAEVKKPGASVKVSCKVSGYSLSKYDMSWVRKAPGKGLEWMGIIYTSGYT<br>DYAQEFQGRVTMTEDTSTDTAYMELSSLRSEDTAVYYCATGNPYYTNGFNSWGQGTL<br>VTVSSASTKGPSVFPLAPSSKSTSGGTAALGCLVKDYFPEPVTVSWNSGALTSGVATGPA<br>VLQSSGLYSLSSVVTVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWYVDGVEVHNAKTKP<br>REEQYNSTYRVVSVLTVLHQDWLNGKEYKCXVSNKALPAPIEKTISKAKGQPREPQVYT<br>LPPSREEMTDNQVSLTCLVKGFYPSDIAVEWESNGQPENNYKTTPPVLMSDGSFFLASKL<br>TVDKSRWQQGNVFSCSVMHEALHNHYTQKSLSLSPGK (wherein X is K or A) |

-continued

| Amino Acid and Nucleotide Sequences |
| --- |

SEQ ID NO: 39
(Human PD-1 amino acid sequence)
MQIPQAPWPVVWAVLQLGWRPGWFLDSPDRPWNPPTFSPALLVVTEGDNATFTCSFSN
TSESFVLNWYRMSPSNQTDKLAAFPEDRSQPGQDCRFRVTQLPNGRDFHMSVVRARRN
DSGTYLCGAISLAPKAQIKESLRAELRVTERRAEVPTAHPSPSPRPAGQFQTLVVGVVGG
LLGSLVLLVWVLAVICSRAARGTIGARRTGQPLKEDPSAVPVFSVDYGELDFQWREKTP
EPPVPCVPEQTEYATIVFPSGMGTSSPARRGSADGPRSAQPLRPEDGHCSWPL SEQ ID NO: 40
(Human PD-1 ECD-His amino acid sequence)
LDSPDRPWNPPTFSPALLVVTEGDNATFTCSFSNTSESFVLNWYRMSPSNQTDKLAAFPE
DRSQPGQDCRFRVTQLPNGRDFHMSVVRARRNDSGTYLCGAISLAPKAQIKESLRAELR
VTERRAEVPTAHPSPSPRPAGQFQHHHHHHHH SEQ ID NO: 41
(Human LAG-3 amino acid sequence)
MWEAQFLGLLFLQPLWVAPVKPLQPGAEVPVVWAQEGAPAQLPCSPTIPLQDLSLLRRA
GVTWQHQPDSGPPAAAPGHPLAPGPHPAAPSSWGPRPRRYTVLSVGPGGLRSGRLPLQP
RVQLDERGRQRGDFSLWLRPARRADAGEYRAAVHLRDRALSCRLRLRLGQASMTASPP
GSLRASDWVILNCSFSRPDRPASVHWFRNRGQGRVPVRESPHHHLAESFLFLPQVSPMD
SGPWGCILTYRDGFNVSIMYNLTVLGLEPPTPLTVYAGAGSRVGLPCRLPAGVGTRSFLT
AKWTPPGGGPDLLVTGDNGDFTLRLEDVSQAQAGTYTCHIHLQEQQLNATVTLAIITVT
PKSFGSPGSLGKLLCEVTPVSGQERFVWSSLDTPSQRSFSGPWLEAQEAQLLSQPWQCQL
YQGERLLGAAVYFTELSSPGAQRSGRAPGALPAGHLLLFLILGVLSLLLLVTGAFGFHLW
RRQWRPRRFSALEQGIHPPQAQSKIEELEQEPEPEPEPEPEPEPEPEPEQL SEQ ID NO: 42
(Human LAG-3 ECD-His amino acid sequence)
LQPGAEVPVVWAQEGAPAQLPCSPTIPLQDLSLLRRAGVTWQHQPDSGPPAAAPGHPLA
PGPHPAAPSSWGPRPRRYTVLSVGPGGLRSGRLPLQPRVQLDERGRQRGDFSLWLRPAR
RADAGEYRAAVHLRDRALSCRLRLRLGQASMTASPPGSLRASDWVILNCSFSRPDRPAS
VHWFRNRGQGRVPVRESPHHHLAESFLFLPQVSPMDSGPWGCILTYRDGFNVSIMYNLT
VLGLEPPTPLTVYAGAGSRVGLPCRLPAGVGTRSFLTAKWTPPGGGPDLLVTGDNGDFT
LRLEDVSQAQAGTYTCHIHLQEQQLNATVTLAIITVTPKSFGSPGSLGKLLCEVTPVSGQE
RFVWSSLDTPSQRSFSGPWLEAQEAQLLSQPWQCQLYQGERLLGAAVYFTELSSPGAQR
SGRAPGALPAGHGGGGSHHHHHH SEQ ID NO: 43
(Cynomolgus LAG-3 ECD-His amino acid sequence)
MWEAQFLGLLFLQPLWVAPVKPPQPGAEISVVWAQEGAPAQLPCSPTIPLQDLSLLRRA
GVTWQHQPDSGPPAPAPGHPPVPGHRPAAPYSWGPRPRRYTVLSVGPGGLRSGRLPLQP
RVQLDERGRQRGDFSLWLRPARRADAGEYRATVHLRDRALSCRLRLRVGQASMTASPP
GSLRTSDWVILNCSFSRPDRPASVHWFRSRGQGRVPVQGSPHHHLAESFLFLPHVGPMD
SGLWGCILTYRDGFNVSIMYNLTVLGLEPATPLTVYAGAGSRVELPCRLPPAVGTQSFLT
AKWAPPGGGPDLLVAGDNGDFTLRLEDVSQAQAGTYICHIRLQGQQLNATVTLAIITVT
PKSFGSPGSLGKLLCEVTPASGQEHFVWSPLNTPSQRSFSGPWLEAQEAQLLSQPWQCQL
HQGERLLGAAVYFTELSSPGAQRSGRAPGALRAGHAAAHHHHHHSGS SEQ ID NO: 44
(LAG-3 HCDR1 amino acid sequence)
TVSGGSISSYYWS SEQ ID NO: 45
(LAG-3 HCDR2 amino acid sequence)
RIFTSGTTNYNPELKS SEQ ID NO: 46
PD1 HCDR2 amino acid sequence)
IIYTSGYTDYAQKFQG SEQ ID NO: 47
(LAG-3 HCDR3 amino acid sequence)
ARYDAFDI SEQ ID NO: 48
(LAG-3 LCDRI amino acid sequence)
RASQSVSSSYLA SEQ ID NO: 49
(LAG-3 LCDR2 amino acid sequence)
YGASSRAT -continued

| Amino Acid and Nucleotide Sequences |
|---|

SEQ ID NO: 50
(LAG-3 LCDR3 amino acid sequence)
QQYGSSPIT

SEQ ID NO: 51
(LAG-3 HCDR1 amino acid sequence)
TVSGGSIHSYYWS

SEQ ID NO: 52
(LAG-3 HCDR2 amino acid sequence)
RIFTSGSTNYNPELKS

SEQ ID NO: 53
(LAG-3 Variable Heavy amino acid sequence)
QVQLQESGPGLVKPSETLSLTCTVSGGSISSYYWSWIRKPAGKGLEWVGRIFTSGTTNYN
PELKSRVTMSVDTSKNQFSLKLSSVTAADTAVYYCARYDAFDIWGQGTLVTVSS SEQ ID NO: 54
(LAG-3 Variable Heavy amino acid sequence)
QVQLQESGPGLVKPSETLSLTCTVSGGSIHSYYWSWIRKPAGKGLEWVGRIFTSGSTNYN
PELKSRVTMSVDTSKNQFSLKLSSVTAADTAVYYCARYDAFDIWGQGTLVTVSS SEQ ID NO: 55
(PD-1 Variable Heavy amino acid sequence)
QVQLVQSGAEVKKPGASVKVSCKVSGYSLSKYDMSWVRYAPGKGLEWMGIIYTSGYT
DYAQKFQGRVTMTEDTSTDTAYMELSSLRSEDTAVYYCATGNPYYTNGFNSWGRGTL
VTVSS SEQ ID NO: 56
(LAG-3 Variable Light amino acid sequence)
RIVLTQSPGTLSLSPGERATLSCRASQSVSSSYLAWFQDKPGQAPRLLIYGASSRATGIPD
RFSGSGSGTDFTLTISRLEPEDFAVYYCQQYGSSPITFGQGTKVEIK SEQ ID NO: 57
(PD-1 Variable Light amino acid sequence)
DIQMTQSPSSLSASVGDRVTITCQASQSPNNLLAWYQRKPGDAPKLLIYGASDLPSGVPS
RFSGSGSGTDFTLTISSLQPEDFATYYCQNNYYVGPVSYAFGGGTKVEIK SEQ ID NO: 58
(LAG-3 Constant Heavy amino acid sequence)
ASTKGPSVFPLAPSSKSTSGGTAALGCLVADYFPEPVTVSWNSGALTSGVHTFPAVLQSS
GLYSLSSVVTVPSSSLGTQTYICNVNHKPSNTKVDERVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCAVSNKALPAPIEKTISKAKGQPREPQVYTLPPSR
GDMTKNQVQLTCLVKGFYPSDIAVEWESNGQPENNYKTTPPVLDSDGSFFLASKLTVDK
SRWQQGNVFSCSVMHEALHNHYTQKSLSLSPGK SEQ ID NO: 59
(PD-1 Constant Heavy amino acid sequence)
ASTKGPSVFPLAPSSKSTSGGTAALGCLVKDYFPEPVTVSWNSGALTSGVATGPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCAVSNKALPAPIEKTISKAKGQPREPQVSTLPPSRE
EMTKNQVSLMCLVYGFYPSDIAVEWESNGQPENNYKTTPPVLDSDGSFFLYSVLTVDKS
RWQQGNVFSCSVMHEALHNHYTQKSLSLSPGK SEQ ID NO: 60
(LAG-3 Constant Light amino acid sequence)
RTVAAPSVFIFPPSDKQLKSGTARVVCLLNNFYPREAKVQWKVDNALQSGNSQESVTEQ
DSKDSTYSLSSTLTLSKADYEKHKVYACEVTHQGLSSPVTKSFNRGEC SEQ ID NO: 61
(LAG-3 Heavy Chain amino acid sequence)
QVQLQESGPGLVKPSETLSLTCTVSGGSISSYYWSWIRKPAGKGLEWVGRIFTSGTTNYN
PELKSRVTMSVDTSKNQFSLKLSSVTAADTAVYYCARYDAFDIWGQGTLVTVSSASTKG
PSVFPLAPSSKSTSGGTAALGCLVADYFPEPVTVSWNSGALTSGVHTFPAVLQSSGLYSL
SSVVTVPSSSLGTQTYICNVNHKPSNTKVDERVEPKSCDKTHTCPPCPAPELLGGPSVFLF
PPKPKDTLMISRTPEVTCVVVDVSHEDPEVKFNWYVDGVEVHNAKTKPREEQYNSTYR
VVSVLTVLHQDWLNGKEYKCAVSNKALPAPIEKTISKAKGQPREPQVYTLPPSRGDMTK
NQVQLTCLVKGFYPSDIAVEWESNGQPENNYKTTPPVLDSDGSFFLASKLTVDKSRWQQ
GNVFSCSVMHEALHNHYTQKSLSLSPGK SEQ ID NO: 62
(LAG-3 Heavy Chain amino acid sequence)
QVQLQESGPGLVKPSETLSLTCTVSGGSIHSYYWSWIRKPAGKGLEWVGRIFTSGSTNYN
PELKSRVTMSVDTSKNQFSLKLSSVTAADTAVYYCARYDAFDIWGQGTLVTVSSASTKG
PSVFPLAPSSKSTSGGTAALGCLVADYFPEPVTVSWNSGALTSGVHTFPAVLQSSGLYSL -continued

| Amino Acid and Nucleotide Sequences |
|---|
| SSVVTVPSSSLGTQTYICNVNHKPSNTKVDERVEPKSCDKTHTCPPCPAPELLGGPSVFLF<br>PPKPKDTLMISRTPEVTCVVVDVSHEDPEVKFNWYVDGVEVHNAKTKPREEQYNSTYR<br>VVSVLTVLHQDWLNGKEYKCAVSNKALPAPIEKTISKAKGQPREPQVYTLPPSRGDMTK<br>NQVQLTCLVKGFYPSDIAVEWESNGQPENNYKTTPPVLDSDGSFFLASKLTVDKSRWQQ<br>GNVFSCSVMHEALHNHYTQKSLSLSPGK |
| SEQ ID NO: 63<br>(PD-1 Heavy Chain amino acid sequence)<br>QVQLVQSGAEVKKPGASVKVSCKVSGYSLSKYDMSWVRYAPGKGLEWMGIIYTSGYT<br>DYAQKFQGRVTMTEDTSTDTAYMELSSLRSEDTAVYYCATGNPYYTNGFNSWGRGTL<br>VTVSSASTKGPSVFPLAPSSKSTSGGTAALGCLVKDYFPEPVTVSWNSGALTSGVATGPA<br>VLQSSGLYSLSSVVTVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWYVDGVEVHNAKTKP<br>REEQYNSTYRVVSVLTVLHQDWLNGKEYKCAVSNKALPAPIEKTISKAKGQPREPQVST<br>LPPSREEMTKNQVSLMCLVYGFYPSDIAVEWESNGQPENNYKTTPPVLDSDGSFFLYSV<br>LTVDKSRWQQGNVFSCSVMHEALHNHYTQKSLSLSPGK |
| SEQ ID NO: 64<br>(LAG-3 Light Chain amino acid)<br>RIVLTQSPGTLSLSPGERATLSCRASQSVSSSYLAWFQDKPGQAPRLLIYGASSRATGIPD<br>RFSGSGSGTDFTLTISRLEPEDFAVYYCQQYGSSPITFGQGTKVEIKRTVAAPSVFIFPPSD<br>KQLKSGTARVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO: 65<br>(PD-1 Light Chain amino acid sequence)<br>DIQMTQSPSSLSASVGDRVTITCQASQSPNNLLAWYQRKPGDAPKLLIYGASDLPSGVPS<br>RFSGSGSGTDFTLTISSLQPEDFATYYCQNNYYVGPVSYAFGGGTKVEIKGQPKAAPSVT<br>LFPPSSEELQANKATLVCYISDFYPGAVTVAWKADSSPVKAGVETTTPSKQSNNKYAAW<br>SYLSLTPEQWKSHRSYSCQVTHEGSTVEKTVAPTEC |
| SEQ ID NO: 66<br>(LAG-3 Heavy Chain DNA sequence)<br>caggtgcagctgcaggagtcgggcccaggactggtgaagccttcggagaccctgtccctcacctgcactgtctctggtggctccatcagta<br>gttactactggagctggatacggaagcccgccgggaagggactggagtgggtcgggcgaatcttcacaagtgggacaaccaactacaac<br>cccgagctcaagagtcgagtcaccatgtcagtagacacgtccaagaaccagttctccctgaagctgagctctgtgaccgctgcggacacgg<br>ccgtgtattactgtgcgagatacgacgcattcgacatatggggacagggaacactagtgacggtctcaagcgctagcaccaagggcccatc<br>ggtcttcccccctggcaccctcctccaagagcacctctgggggcacagcggccctgggctgcctggtcgccgactacttccccgaaccggt<br>gacggtgtcgtggaactcaggcgccctgaccagcggcgtgcacaccttcccggctgtcctacagtcctcaggactctactccctcagcagc<br>gtggtgaccgtgccctccagcagcttgggcacccagacctacatctgcaacgtgaatcacaagcccagcaacaccaaggtggacgagag<br>agttgagcccaaatcttgtgacaaaactcacacatgcccaccgtgcccagcacctgaactcctggggggaccgtcagtcttcctcttccccc<br>caaaacccaaggacaccctcatgatctcccggacccctgaggtcacatgcgtggtggtggacgtgagccacgaagaccctgaggtcaagt<br>tcaactggtatgtggacggcgtggaggtgcataatgccaagacaaagccgcgggaggagcagtacaacagcacgtaccgtgtggtcagc<br>gtcctcaccgtcctgcaccaagactggctgaatggcaaggagtacaagtgcgccgtctccaacaaagccctcccagcccccatcgagaaa<br>accatctccaaagccaaagggcagccccgagaaccacaggtgtacaccctgcccccatcccgggggggacatgaccaagaaccaagtcc<br>agctgacctgcctggtcaaaggcttctatcccagcgacatcgccgtggagtgggagagcaatgggcagccggagaacaactacaagacc<br>acgcctcccgtgctggactccgacggctccttcttcctcgcttccaagctcaccgtggacaagagcaggtggcagcaggggaacgtcttctc<br>atgctccgtgatgcatgaggctctgcacaaccactacacgcagaagagcctctccctgtctccgggcaaa |
| SEQ ID NO: 67<br>(LAG-3 Heavy Chain DNA sequence)<br>caggtgcagctgcaggagtcgggcccaggactggtgaagccttcggagaccctgtccctcacctgcactgtctctggtggctccatccaca<br>gttactactggagctggatacggaagcccgccgggaagggactggagtgggtcgggcgaatcttcacaagtgggtccaccaactacaac<br>cccgagctcaagagtcgagtcaccatgtcagtagacacgtccaagaaccagttctccctgaagctgagctctgtgaccgctgcggacacgg<br>ccgtgtattactgtgcgagatacgacgcattcgacatatggggacagggaacactagtgacggtctcaagcgctagcaccaagggcccatc<br>ggtcttcccccctggcaccctcctccaagagcacctctgggggcacagcggccctgggctgcctggtcgccgactacttccccgaaccggt<br>gacggtgtcgtggaactcaggcgccctgaccagcggcgtgcacaccttcccggctgtcctacagtcctcaggactctactccctcagcagc<br>gtggtgaccgtgccctccagcagcttgggcacccagacctacatctgcaacgtgaatcacaagcccagcaacaccaaggtggacgagag<br>agttgagcccaaatcttgtgacaaaactcacacatgcccaccgtgcccagcacctgaactcctggggggaccgtcagtcttcctcttccccc<br>caaaacccaaggacaccctcatgatctcccggacccctgaggtcacatgcgtggtggtggacgtgagccacgaagaccctgaggtcaagt<br>tcaactggtatgtggacggcgtggaggtgcataatgccaagacaaagccgcgggaggagcagtacaacagcacgtaccgtgtggtcagc<br>gtcctcaccgtcctgcaccaagactggctgaatggcaaggagtacaagtgcgccgtctccaacaaagccctcccagcccccatcgagaaa<br>accatctccaaagccaaagggcagccccgagaaccacaggtgtacaccctgcccccatcccgggggggacatgaccaagaaccaagtcc<br>agctgacctgcctggtcaaaggcttctatcccagcgacatcgccgtggagtgggagagcaatgggcagccggagaacaactacaagacc<br>acgcctcccgtgctggactccgacggctccttcttcctcgcttccaagctcaccgtggacaagagcaggtggcagcaggggaacgtcttctc<br>atgctccgtgatgcatgaggctctgcacaaccactacacgcagaagagcctctccctgtctccgggcaaa |
| SEQ ID NO: 68<br>(PD-1 Heavy Chain DNA sequence)<br>caagtgcagttggtgcagtcggggggcagaagtgaaaaagcccggcgcttcggtgaaagtgtcctgcaaagtgtccggctattctttgagca<br>aatacgacatgtcatgggtcagaTACgctcccggaaagggtctggagtggatggggattatctatacatccggctacaccgattacgccc<br>aaaagttccaggggagagtcaccatgactgaggatacgtccaccgacaccgcctacatggaactgtccagcctgcggtccgaggacactg<br>cggtgtactactgcgcgaccggaaacccatactacaccaatggattcaatagctggggaAGAggtactcttgtgacggtgtccagcgcta<br>gcaccaagggcccatcggtcttcccccctggcaccctcctccaagagcacctctgggggcacagcggccctgggctgcctggtcaaggact<br>acttccccgaaccggtgacggtgtcgtggaactcaggcgccctgaccagcggcgtggccaccggcccggctgtcctacagtcctcagga<br>ctctactccctcagcagcgtggtgaccgtgccctccagcagcttgggcacccagacctacatctgcaacgtgaatcacaagcccagcaaca<br>ccaaggtggacaagagagttgagcccaaatcttgtgacaaaactcacacatgcccaccgtgcccagcacctgaactcctggggggaccgt |

-continued

Amino Acid and Nucleotide Sequences

```
cagtcttcctcttccccccaaaacccaaggacaccctcatgatctcccggacccctgaggtcacatgcgtggtggtggacgtgagccacga
agaccctgaggtcaagttcaactggtatgtggacggcgtggaggtgcataatgccaagacaaagccgcgggaggagcagtacaacagca
cgtaccgtgtggtcagcgtcctcaccgtcctgcaccaagactggctgaatggcaaggagtacaagtgcGCCgtctccaacaaagccctc
ccagcccccatcgagaaaaccatctccaaagccaaagggcagccccgagaaccacaggtgtccaccctgcccccatcccgggaggaga
tgaccaagaaccaagtcagcctgatgtgcctggtctatggcttctatcccagcgacatcgccgtggagtgggagagcaatgggcagccgg
agaacaactacaagaccacgcctcccgtgctggactccgacggctccttcttcctctattccgtgctcaccgtggacaagagcaggtggcag
caggggaacgtcttctcatgctccgtgatgcatgaggctctgcacaaccactacacgcagaagagcctctccctgtctccgggcaaa
```

SEQ ID NO: 69
(LAG-3 Light Chain DNA sequence)

```
Agaattgtgttgacgcagtctccaggcaccctgtctttgtctccaggggaaagagccaccctctcctgcagggccagtcagagtgttagcag
cagctacttagcctggttccaggacaaacctggccaggctcccaggctcctcatctatggtgcatccagcagggccactggcatcccagac
aggttcagtggcagtgggtctgggacagacttcactctcaccatcagcagactggagcctgaagattttgcagtgtattactgtcagcagtac
ggaagcagtccgataacgttcggccagggaacaaaggtggaaataaagcggaccgtggctgcaccatctgtcttcatcttcccgccatctg
ataagcagttgaaatctggaactgccagagttgtgtgcctgctgaataacttctatcccagagaggccaaagtaccynoagtggaaggtgga
taacgccctccaatcgggtaactcccaggagagtgtcacagagcaggacagcaaggacagcacctacagcctcagcagcaccctgacgc
tgagcaaagcagactacgagaaacacaaagtctacgcctgcgaagtcacccatcagggcctgagctcgcccgtcacaaagagcttcaaca
ggggagagtgc
```

SEQ ID NO: 70
(PD-1 Light Chain DNA sequence)

```
gacatccagatgacccagtctccatcctccctgtctgcatctgtgggagacagagtcaccatcacttgccaggccagtcagagccctaataa
cctcctggcctggtatcagAGAaaaccagggGACgcccctaagctcctgatctatggtgcatccgatctgccatctggggtcccatcaa
ggttcagtggcagtggatctgggacagatttcactctcaccatcagcagtctgcaacctgaagattttgcaacttactactgtcagaacaattatt
atgtgggaccagtgagctatgctttcggcggagggaccaaggtggagatcaagggccagcctaaagctgcccctagcgttacccttttccc
accgagctccgaggagctgcaggccaataaagcaaccttggtctgctacatatcagattttaccctggcgccgtgaccgtagcatggaaag
ctgattcatcccctgtgaaggccggtgttgaaactacaaccccttccaaacaatctaacaataaatacgcggcatggtcctacctgtccttgac
acccgagcagtggaaatctcacagatcttacagctgccaggtcacccacgaggggagcactgtggagaagaccgtcgcgcccactgagt
gc
```

We claim:

1. An antibody that comprises a human LAG-3 binding domain comprising a heavy chain variable region (VH) and a light chain variable region (VL), wherein the VH comprises heavy chain complementarity determining regions (HCDR): HCDR1 comprising SEQ ID NO: 1, HCDR2 comprising SEQ ID NO: 2, and HCDR3 comprising SEQ ID NO: 3; and wherein the VL comprises light chain complementarity determining regions (LCDR): LCDR1 comprising SEQ ID NO: 4, LCDR2 comprising SEQ ID NO: 5, and LCDR3 comprising SEQ ID NO: 6.

2. The antibody of claim 1, wherein the VH comprises SEQ ID NO: 13 and the VL comprises SEQ ID NO: 14.

3. The antibody of claim 1, wherein the antibody comprises a light chain (LC) comprising SEQ ID NO: 22, and a heavy chain (HC) comprising SEQ ID NO: 37.

4. The antibody of claim 3, wherein X at position 328 in SEQ ID NO: 37 is a lysine residue.

5. The antibody of claim 3, wherein X at position 328 in SEQ ID NO: 37 is an alanine residue.

6. The antibody of claim 3 wherein the antibody comprises (a) an LC comprising SEQ ID NO: 22, and (b) an HC comprising SEQ ID NO: 21.

7. The antibody of claim 3 wherein the antibody comprises (a) an LC comprising SEQ ID NO: 22, and (b) an HC comprising SEQ ID NO: 31.

8. The antibody of claim 1, wherein the antibody is a human IgG1 or IgG4 isotype.

9. The antibody of claim 8, wherein the antibody is a human IgG1 isotype.

10. The antibody of claim 1, wherein the antigen binding domain is a single-chain variable fragment (scFv).

11. A nucleic acid comprising a sequence encoding one or both of SEQ ID NO: 22 and SEQ ID NO: 37.

12. The nucleic acid of claim 11, wherein X at position 328 in SEQ ID NO: 37 is a lysine residue.

13. The nucleic acid of claim 11, wherein X at position 328 in SEQ ID NO: 37 is an alanine residue.

14. A vector comprising the nucleic acid of claim 11.

15. A cell comprising the vector of claim 14.

16. The cell of claim 15, wherein the cell is a mammalian cell.

17. A composition comprising the antibody of claim 1.

18. A human LAG-3/human PD-1 dual agonist bispecific antibody comprising:

(a) a first antigen binding domain that binds human LAG-3 comprising a first heavy chain variable region (VH1) and a first light chain variable region (VL1), wherein the VH1 comprises: HCDR1 comprising SEQ ID NO: 1, HCDR2 comprising SEQ ID NO: 2, and HCDR3 comprising SEQ ID NO: 3; and wherein the VL1 comprises: LCDR1 comprising SEQ ID NO: 4, LCDR2 comprising SEQ ID NO: 5, and LCDR3 comprising SEQ ID NO: 6; and (b) a second antigen binding domain that binds human PD-1 comprising a second heavy chain variable region (VH2) and a second light chain variable region (VL2), wherein the VH2 comprises: HCDR1 comprising SEQ ID NO: 7, HCDR2 comprising SEQ ID NO: 8, and HCDR3 comprising SEQ ID NO: 9; and wherein the VL2 comprises LCDR1 comprising SEQ ID NO: 10, LCDR2 comprising SEQ ID NO: 11, and LCDR3 comprising SEQ ID NO: 12.

19. The human LAG-3/human PD-1 dual agonist bispecific antibody of claim 18, wherein the VH1 comprises SEQ ID NO: 13 and the VL1 comprises SEQ ID NO: 14.

20. The human LAG-3/human PD-1 dual agonist bispecific antibody of claim 18, wherein the VH2 comprises SEQ ID NO: 17 and the VL2 comprises SEQ ID NO: 18.

21. The human LAG-3/human PD-1 dual agonist bispecific antibody of claim 18, wherein the antibody comprises two heavy chains and two light chains, wherein the first heavy chain (HC1) comprises the first VH1 and a first heavy chain constant region, the first light chain (LC1) comprises the VL1 and a first light chain constant region, the second heavy chain (HC2) comprises the second VH2 and a second heavy chain constant region, and the second light chain (LC2) comprises the second VL2 and a second light chain constant region.

22. The human LAG-3/human PD-1 dual agonist bispecific antibody of claim 18, wherein bispecific antibody comprises a first HC1 comprising SEQ ID NO: 21, a first LC1 comprising SEQ ID NO: 22, a second HC1 comprises SEQ ID NO: 23, and a second LC1 comprising SEQ ID NO: 24.

23. The human LAG-3/human PD-1 dual agonist bispecific antibody of claim 22, wherein the HC1 comprises SEQ ID NO: 37, the LC1 comprises SEQ ID NO: 22, the HC2 comprises SEQ ID NO: 38, and the LC2 comprises SEQ ID NO: 24.

24. The human LAG-3/human PD-1 dual agonist bispecific antibody of claim 23, wherein X at position 328 in SEQ ID NO: 37 is alanine, and X at position 324 in SEQ ID NO: 38 is alanine.

25. The human LAG-3/human PD-1 dual agonist bispecific antibody of claim 23, wherein X at position 328 in SEQ ID NO: 37 is lysine, and X at position 324 in SEQ ID NO: 38 is lysine.

26. The human LAG-3/human PD-1 dual agonist bispecific antibody of claim 18, wherein bispecific antibody comprises a first HC1 comprising SEQ ID NO: 31, a first LC1 comprising SEQ ID NO: 22, a second HC1 comprising SEQ ID NO: 32, and a second LC1 comprising SEQ ID NO: 24.

27. A nucleic acid comprising a sequence encoding one or more of SEQ ID NOS: 22, 24, 37, and 38, wherein if amino acid residue 328 in SEQ ID NO: 37 is a lysine residue, then X at position 324 in SEQ ID NO: 38 is a lysine residue, and wherein if X at position 328 in SEQ ID NO: 37 is an alanine residue, then X at position 324 in SEQ ID NO: 38 is an alanine residue.

28. A cell comprising a nucleic acid comprising a sequence encoding one or more of the polypeptides of SEQ ID NOS: 22, 24, 37 and 38, wherein if X at position 328 in SEQ ID NO: 37 is a lysine residue, then X at position 324 in SEQ ID NO: 38 is a lysine residue, and wherein if X at position 328 in SEQ ID NO: 37 is an alanine residue, then X at position 324 in SEQ ID NO: 38 is an alanine residue, and wherein the cell is capable of expressing the one or more polypeptides.

29. The cell of claim 28, wherein the cell is a mammalian cell.

30. A process of producing a human LAG-3/human PD-1 dual agonist antibody, comprising culturing the cell of claim 29 under conditions such that the antibody is expressed, and recovering the expressed antibody from the culture medium.

31. A human LAG-3/human PD-1 dual agonist antibody produced by culturing the cell of claim 30 under conditions such that the antibody is expressed, and recovering the expressed antibody from the culture medium.

32. A pharmaceutical composition comprising the human LAG-3/human PD-1 dual agonist antibody of claim 18, and a pharmaceutically acceptable excipient, diluent or carrier.

33. A method of treating autoimmune disease in a subject in need thereof, comprising administering to the subject a therapeutically effective amount of the human LAG-3/human PD-1 dual agonist bispecific antibody of claim 18.

34. The method of claim 33, wherein the autoimmune disease is rheumatoid arthritis, ulcerative colitis, Type I diabetes mellitus, or systemic lupus erythematosus.

* * * * *

SEQUENCE LISTING

```
Sequence total quantity: 43
SEQ ID NO: 1            moltype = AA  length = 13
FEATURE                 Location/Qualifiers
source                  1..13
                        mol_type = protein
                        organism = synthetic construct
SEQUENCE: 1
KASGYTFTGY YMH                                                      13

SEQ ID NO: 2            moltype = AA  length = 17
FEATURE                 Location/Qualifiers
source                  1..17
                        mol_type = protein
                        organism = synthetic construct
SEQUENCE: 2
WINPNSGDTN YAQKFQG                                                  17

SEQ ID NO: 3            moltype = AA  length = 16
FEATURE                 Location/Qualifiers
source                  1..16
                        mol_type = protein
                        organism = synthetic construct
SEQUENCE: 3
AREGDSSGWH GGWFDP                                                   16

SEQ ID NO: 4            moltype = AA  length = 17
FEATURE                 Location/Qualifiers
source                  1..17
                        mol_type = protein
                        organism = synthetic construct
SEQUENCE: 4
RSSQSLLDSA EGSTYLD                                                  17

SEQ ID NO: 5            moltype = AA  length = 8
FEATURE                 Location/Qualifiers
source                  1..8
                        mol_type = protein
                        organism = synthetic construct
SEQUENCE: 5
YTLSYRAS                                                            8
```

```
SEQ ID NO: 6            moltype = AA  length = 9
FEATURE                 Location/Qualifiers
source                  1..9
                        mol_type = protein
                        organism = synthetic construct
SEQUENCE: 6
MQRVEFPYT                                                          9

SEQ ID NO: 7            moltype = AA  length = 13
FEATURE                 Location/Qualifiers
source                  1..13
                        mol_type = protein
                        organism = synthetic construct
SEQUENCE: 7
KVSGYSLSKY DMS                                                     13

SEQ ID NO: 8            moltype = AA  length = 16
FEATURE                 Location/Qualifiers
source                  1..16
                        mol_type = protein
                        organism = synthetic construct
SEQUENCE: 8
IIYTSGYTDY AQEFQG                                                  16

SEQ ID NO: 9            moltype = AA  length = 13
FEATURE                 Location/Qualifiers
source                  1..13
                        mol_type = protein
                        organism = synthetic construct
SEQUENCE: 9
ATGNPYYTNG FNS                                                     13

SEQ ID NO: 10           moltype = AA  length = 11
FEATURE                 Location/Qualifiers
source                  1..11
                        mol_type = protein
                        organism = synthetic construct
SEQUENCE: 10
QASQSPNNLL A                                                       11

SEQ ID NO: 11           moltype = AA  length = 8
FEATURE                 Location/Qualifiers
source                  1..8
                        mol_type = protein
                        organism = synthetic construct
SEQUENCE: 11
YGASDLPS                                                           8

SEQ ID NO: 12           moltype = AA  length = 12
FEATURE                 Location/Qualifiers
source                  1..12
                        mol_type = protein
                        organism = synthetic construct
SEQUENCE: 12
QNNYYVGPVS YA                                                      12

SEQ ID NO: 13           moltype = AA  length = 123
FEATURE                 Location/Qualifiers
source                  1..123
                        mol_type = protein
                        organism = synthetic construct
SEQUENCE: 13
QVQLVQSGAE VKKPGASVKV SCKASGYTFT GYYMHWVRYA PGQGLEWMGW INPNSGDTNY  60
AQKFQGRVTM TRDTSISTAY MELSRLRSDD TAVYYCAREG DSSGWHGGWF DPWGRGTLVT  120
VSS                                                                123

SEQ ID NO: 14           moltype = AA  length = 113
FEATURE                 Location/Qualifiers
source                  1..113
                        mol_type = protein
                        organism = synthetic construct
SEQUENCE: 14
DIVMTQTPLS LPVTPGEPAS ISCRSSQSLL DSAEGSTYLD WFLRKPGDSP QLLIYTLSYR  60
ASGVPDRFSG SGSGTDFTLK ISRVEAEDVG VYYCMQRVEF PYTFGQGTKV EIK         113

SEQ ID NO: 15           moltype = AA  length = 330
FEATURE                 Location/Qualifiers
source                  1..330
                        mol_type = protein
```

```
                         organism = synthetic construct
SEQUENCE: 15
ASTKGPSVFP LAPCSKSTSG GTAALGCLVK DYFPEPVTVS WNSGALTSGV HTFPAVLQSS  60
GLYSLSSVVT VPSSSLGTQT YICNVNHKPS NTKVDKRVEP DSGDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPRRPR VYTLPPSREE  240
MTKNQVSLVC LVKGFYPSDI AVEWESNGQP ENNYKTTPPV LDSDGSFFLY SVLTVDKSRW  300
QQGNVFSCSV MHEALHNHYT QKSLSLSPGK                                   330

SEQ ID NO: 16            moltype = AA  length = 107
FEATURE                  Location/Qualifiers
source                   1..107
                         mol_type = protein
                         organism = synthetic construct
SEQUENCE: 16
RTVAAPSVFI FPPSKEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 17            moltype = AA  length = 119
FEATURE                  Location/Qualifiers
source                   1..119
                         mol_type = protein
                         organism = synthetic construct
SEQUENCE: 17
QVQLVQSGAE VKKPGASVKV SCKVSGYSLS KYDMSWVRKA PGKGLEWMGI IYTSGYTDYA  60
QEFQGRVTMT EDTSTDTAYM ELSSLRSEDT AVYYCATGNP YYTNGFNSWG QGTLVTVSS   119

SEQ ID NO: 18            moltype = AA  length = 110
FEATURE                  Location/Qualifiers
source                   1..110
                         mol_type = protein
                         organism = synthetic construct
SEQUENCE: 18
RIQMTQSPSS LSASVGDRVT ITCQASQSPN NLLAWYQDKP GKAPKLLIYG ASDLPSGVPS  60
RFSGSGSGTD FTLTISSLQP EDFATYYCQN NYYVGPVSYA FGGGTKVEIK             110

SEQ ID NO: 19            moltype = AA  length = 330
FEATURE                  Location/Qualifiers
source                   1..330
                         mol_type = protein
                         organism = synthetic construct
SEQUENCE: 19
ASTKGPSVFP LAPSSKSTSG GTAALGCLVK DYFPEPVTVS WNSGALTSGV ATGPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTDNQVSLTC LVKGFYPSDI AVEWESNGQP ENNYKTTPPV LMSDGSFFLA SKLTVDKSRW  300
QQGNVFSCSV MHEALHNHYT QKSLSLSPGK                                   330

SEQ ID NO: 20            moltype = AA  length = 105
FEATURE                  Location/Qualifiers
source                   1..105
                         mol_type = protein
                         organism = synthetic construct
SEQUENCE: 20
GQPKAAPSVT LFPPSSEELQ ANKATLVCYI SDFYPGAVTV AWKADSSPVK AGVETTTPSK  60
QSNNKYAAWS YLSLTPEQWK SHRSYSCQVT HEGSTVEKTV APTEC                  105

SEQ ID NO: 21            moltype = AA  length = 453
FEATURE                  Location/Qualifiers
source                   1..453
                         mol_type = protein
                         organism = synthetic construct
SEQUENCE: 21
QVQLVQSGAE VKKPGASVKV SCKASGYTFT GYYMHWVRYA PGQGLEWMGW INPNSGDTNY  60
AQKFQGRVTM TRDTSISTAY MELSRLRSDD TAVYYCAREG DSSGWHGGWF DPWGRGTLVT  120
VSSASTKGPS VFPLAPCSKS TSGGTAALGC LVKDYFPEPV TVSWNSGALT SGVHTFPAVL  180
QSSGLYSLSS VVTVPSSSLG TQTYICNVNH KPSNTKVDKR VEPDSGDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR RPRVYTLPPS  360
REEMTKNQVS LVCLVKGFYP SDIAVEWESN GQPENNYKTT PPVLDSDGSF FLYSVLTVDK  420
SRWQQGNVFS CSVMHEALHN HYTQKSLSLS PGK                               453

SEQ ID NO: 22            moltype = AA  length = 220
FEATURE                  Location/Qualifiers
source                   1..220
                         mol_type = protein
                         organism = synthetic construct
SEQUENCE: 22
```

```
DIVMTQTPLS LPVTPGEPAS ISCRSSQSLL DSAEGSTYLD WFLRKPGDSP QLLIYTLSYR  60
ASGVPDRFSG SGSGTDFTLK ISRVEAEDVG VYYCMQRVEF PYTFGQGTKV EIKRTVAAPS  120
VFIFPPSKEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 23          moltype = AA  length = 449
FEATURE                Location/Qualifiers
source                 1..449
                       mol_type = protein
                       organism = synthetic construct
SEQUENCE: 23
QVQLVQSGAE VKKPGASVKV SCKVSGYSLS KYDMSWVRKA PGKGLEWMGI IYTSGYTDYA  60
QEFQGRVTMT EDTSTDTAYM ELSSLRSEDT AVYYCATGNP YYTNGFNSWG QGTLVTVSSA  120
STKGPSVFPL APSSKSTSGG TAALGCLVKD YFPEPVTVSW NSGALTSGVA TGPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TDNQVSLTCL VKGFYPSDIA VEWESNGQPE NNYKTTPPVL MSDGSFFLAS KLTVDKSRWQ  420
QGNVFSCSVM HEALHNHYTQ KSLSLSPGK                                    449

SEQ ID NO: 24          moltype = AA  length = 215
FEATURE                Location/Qualifiers
source                 1..215
                       mol_type = protein
                       organism = synthetic construct
SEQUENCE: 24
RIQMTQSPSS LSASVGDRVT ITCQASQSPN NLLAWYQDKP GKAPKLLIYG ASDLPSGVPS  60
RFSGSGSGTD FTLTISSLQP EDFATYYCQN NYYVGPVSYA FGGGTKVEIK GQPKAAPSVT  120
LFPPSSEELQ ANKATLVCYI SDFYPGAVTV AWKADSSPVK AGVETTTPSK QSNNKYAAWS  180
YLSLTPEQWK SHRSYSCQVT HEGSTVEKTV APTEC                             215

SEQ ID NO: 25          moltype = DNA  length = 1359
FEATURE                Location/Qualifiers
source                 1..1359
                       mol_type = other DNA
                       organism = synthetic construct
SEQUENCE: 25
caggtgcagc tggtgcagtc tggggctgag gtgaagaagc ctggggcctc agtgaaggtc  60
tcctgcaagg cttctggata caccttcacc ggctactata tgcactgggt gcgatacgcc  120
cctggacaag ggcttgagtg gatgggatgg atcaacccta acagtggtga cacaaactat  180
gcacagaagt ttcagggcag ggtcaccatg accagggaca cgtccatcag cacagcctac  240
atggagctga gcaggctgag atctgacgac acggccgtgt attactgtgc gagagaaggg  300
gactcatcag gatggcacgg agggtggttc gacccctggg gaagaggaac actggtgacg  360
gtgagctcgg ctagcaccaa gggcccatcg gtcttccccc tggcaccctg ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaga  660
gttgagcccg actctggcga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt atgtggacgg cgtggaggtg cataatgcca agacaaagcc gcgggaggag  900
cagtacaaca gcacgtaccg tgtggtcagc gtcctcaccg tcctgcacca agactggctg  960
aatggcaagg agtacaagtg caaggtctcc aacaaagccc tcccagcccc catcgagaaa  1020
accatctcca aagccaaagg gcagccccga agaccacggg tgtacaccct gcccccatcc  1080
cgggaggaga tgaccaagaa ccaagtcagc ctggtctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctatt ccgtgctcac cgtggacaag  1260
agcaggtggc agcaggggaa cgtcttctca tgctccgtga tgcatgaggc tctgcacaac  1320
cactacacgc agaagagcct ctccctgtct ccgggcaaa                         1359

SEQ ID NO: 26          moltype = DNA  length = 660
FEATURE                Location/Qualifiers
source                 1..660
                       mol_type = other DNA
                       organism = synthetic construct
SEQUENCE: 26
gatattgtga tgacccagac tccactctcc ctgcccgtca cccctggaga gccggcctcc  60
atctcctgca ggtctagtca gagcctcttg gatagtgctg aaggaagcac ctatttggac  120
tggttcctga gaaagccagg ggactctcca cagctcctga tctatacgct ttcctaccgg  180
gcctctggag tcccagacag gttcagtggc agtgggtcag gcactgattt cacactgaaa  240
atcagcaggg tggaggctga ggatgttgga gtttattact gcatgcagag ggtagaattt  300
ccgtacacat tcggacaggg aacaaaggtg gaaatcaagc ggaccgtggc tgcaccatct  360
gtcttcatct tcccgccatc taaggagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgc  660
```

-continued

```
SEQ ID NO: 27          moltype = DNA  length = 1347
FEATURE                Location/Qualifiers
source                 1..1347
                       mol_type = other DNA
                       organism = synthetic construct
SEQUENCE: 27
caagtgcagt tggtgcagtc gggggcagaa gtgaaaaagc ccggcgcttc ggtgaaagtg  60
tcctgcaaag tgtccggcta ttctttgagc aaatacgaca tgtcatgggt cagaaaggct  120
cccggaaagg gtctggagtg gatggggatt atctatacat ccggctacac cgattacgcc  180
caagagttcc aggggagagt caccatgact gaggatacgt ccaccgacac cgcctacatg  240
gaactgtcca gcctgcggtc cgaggacact gcggtgtact actgcgcgac cggaaaccca  300
tactacacca atggattcaa tagctgggga cagggtactc ttgtgacggt gtccagcgct  360
agcaccaagg gcccatcggt cttcccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtggcc accggcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct gggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtat  840
gtggacggcg tggaggtgca taatgccaag acaaagccgc gggaggagca gtacaacagc  900
acgtaccgtg tggtcagcgt cctcaccgtc ctgcaccaag actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accgacaacc aagtcagcct gacctgcctg gtcaaaggct tctatcccag cgacatcgcc  1140
gtggagtggg agagcaatgg gcagccggag aacaactaca agaccacgcc tcccgtgctg  1200
atgtccgacg gctccttctt cctcgcctcc aagctcaccg tggacaagag caggtggcag  1260
caggggaacg tcttctcatg ctccgtgatg catgaggctc tgcacaacca ctacacgcag  1320
aagagcctct ccctgtctcc gggcaaa                                    1347

SEQ ID NO: 28          moltype = DNA  length = 645
FEATURE                Location/Qualifiers
source                 1..645
                       mol_type = other DNA
                       organism = synthetic construct
SEQUENCE: 28
agaatccaga tgacccagtc tccatcctcc ctgtctgcat ctgtgggaga cagagtcacc  60
atcacttgcc aggccagtca gagccctaat aacctcctgg cctggtatca ggacaaacca  120
gggaaagccc ctaagctcct gatctatggt gcatccgatc tgccatctgg ggtcccatca  180
aggttcagtg gcagtggatc tgggacagat ttcactctca ccatcagcag tctgcaacct  240
gaagattttg caacttacta ctgtcagaac aattattatg tgggaccagt gagctatgct  300
ttcggcggag ggaccaaggt ggagatcaag ggccagccta aagctgcccc tagcgttacc  360
cttttcccac cgagctccga ggagctgcag gccaataaag caaccttggt ctgctacata  420
tcagattttt accctggcgc cgtgaccgta gcatggaaag ctgattcatc ccctgtgaag  480
gccggtgttg aaactacaac cccttccaaa caatctaaca ataaatacgc ggcatggtcc  540
tacctgtcct tgacacccga gcagtggaaa tctcacagat cttacagctg ccaggtcacc  600
cacgagggga gcactgtgga gaagaccgtc gcgcccactg agtgc                645

SEQ ID NO: 29          moltype = AA  length = 330
FEATURE                Location/Qualifiers
source                 1..330
                       mol_type = protein
                       organism = synthetic construct
SEQUENCE: 29
ASTKGPSVFP LAPCSKSTSG GTAALGCLVK DYFPEPVTVS WNSGALTSGV HTFPAVLQSS  60
GLYSLSSVVT VPSSSLGTQT YICNVNHKPS NTKVDKRVEP DSGDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCAVSNKA LPAPIEKTIS KAKGQPRRPR VYTLPPSREE  240
MTKNQVSLVC LVKGFYPSDI AVEWESNGQP ENNYKTTPPV LDSDGSFFLY SVLTVDKSRW  300
QQGNVFSCSV MHEALHNHYT QKSLSLSPGK                                  330

SEQ ID NO: 30          moltype = AA  length = 330
FEATURE                Location/Qualifiers
source                 1..330
                       mol_type = protein
                       organism = synthetic construct
SEQUENCE: 30
ASTKGPSVFP LAPSSKSTSG GTAALGCLVK DYFPEPVTVS WNSGALTSGV ATGPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCAVSNKA LPAPIEKTIS KAKGQPREPQ VYTLPPSREE  240
MTDNQVSLTC LVKGFYPSDI AVEWESNGQP ENNYKTTPPV LMSDGSFFLA SKLTVDKSRW  300
QQGNVFSCSV MHEALHNHYT QKSLSLSPGK                                  330

SEQ ID NO: 31          moltype = AA  length = 453
FEATURE                Location/Qualifiers
source                 1..453
                       mol_type = protein
                       organism = synthetic construct
```

```
SEQUENCE: 31
QVQLVQSGAE VKKPGASVKV SCKASGYTFT GYYMHWVRYA PGQGLEWMGW INPNSGDTNY  60
AQKFQGRVTM TRDTSISTAY MELSRLRSDD TAVYYCAREG DSSGWHGGWF DPWGRGTLVT  120
VSSASTKGPS VFPLAPCSKS TSGGTAALGC LVKDYFPEPV TVSWNSGALT SGVHTFPAVL  180
QSSGLYSLSS VVTVPSSSLG TQTYICNVNH KPSNTKVDKR VEPDSGDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCAVS NKALPAPIEK TISKAKGQPR RPRVYTLPPS  360
REEMTKNQVS LVCLVKGFYP SDIAVEWESN GQPENNYKTT PPVLDSDGSF FLYSVLTVDK  420
SRWQQGNVFS CSVMHEALHN HYTQKSLSLS PGK                               453

SEQ ID NO: 32          moltype = AA  length = 449
FEATURE                Location/Qualifiers
source                 1..449
                       mol_type = protein
                       organism = synthetic construct
SEQUENCE: 32
QVQLVQSGAE VKKPGASVKV SCKVSGYSLS KYDMSWVRKA PGKGLEWMGI IYTSGYTDYA  60
QEFQGRVTMT EDTSTDTAYM ELSSLRSEDT AVYYCATGNP YYTNGFNSWG QGTLVTVSSA  120
STKGPSVFPL APSSKSTSGG TAALGCLVKD YFPEPVTVSW NSGALTSGVA TGPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCAVSNKAL PAPIEKTISK AKGQPREPQV YTLPPSREEM  360
TDNQVSLTCL VKGFYPSDIA VEWESNGQPE NNYKTTPPVL MSDGSFFLAS KLTVDKSRWQ  420
QGNVFSCSVM HEALHNHYTQ KSLSLSPGK                                    449

SEQ ID NO: 33          moltype = DNA  length = 1359
FEATURE                Location/Qualifiers
source                 1..1359
                       mol_type = other DNA
                       organism = synthetic construct
SEQUENCE: 33
caggtgcagc tggtgcagtc tggggctgag gtgaagaagc ctggggcctc agtgaaggtc  60
tcctgcaagg cttctggata caccttcacc ggctactata tgcactgggt gcgatacgcc  120
cctggacaag ggcttgagtg gatgggatgg atcaacccta acagtggtga cacaaactat  180
gcacagaagt ttcagggcag ggtcaccatg accagggaca cgtccatcag cacagcctac  240
atggagctga gcaggctgag atctgacgac acggccgtgt attactgtgc gagagaaggg  300
gactcatcag gatggcacgg agggtggttc gacccctggg gaagaggaac actggtgacg  360
gtgagctcgg ctagcaccaa gggcccatcg gtcttccccc tggcaccctg ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaga  660
gttgagcccg actctggcga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt atgtggacgg cgtggaggtg cataatgcca agacaaagcc gcgggaggag  900
cagtacaaca gcacgtaccg tgtggtcagc gtcctcaccg tcctgcacca agactggctg  960
aatggcaagg agtacaagtg cgccgtctcc aacaaagccc tcccagcccc catcgagaaa  1020
accatctcca aagccaaagg gcagccccga agaccacggg tgtacaccct gcccccatcc  1080
cgggaggaga tgaccaagaa ccaagtcagc ctggtctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctatt ccgtgctcac cgtggacaag  1260
agcaggtggc agcaggggaa cgtcttctca tgctccgtga tgcatgaggc tctgcacaac  1320
cactacacgc agaagagcct ctccctgtct ccgggcaaa                         1359

SEQ ID NO: 34          moltype = DNA  length = 1347
FEATURE                Location/Qualifiers
source                 1..1347
                       mol_type = other DNA
                       organism = synthetic construct
SEQUENCE: 34
caagtgcagt tggtgcagtc gggggcagaa gtgaaaaagc ccggcgcttc ggtgaaagtg  60
tcctgcaaag tgtccggcta ttctttgagc aaatacgaca tgtcatgggt cagaaaggct  120
cccggaaagg gtctggagtg gatggggatt atctatacat ccggctacac cgattacgcc  180
caagagttcc aggggagagt caccatgact gaggatacgt ccaccgacac cgcctacatg  240
gaactgtcca gcctgcggtc cgaggacact gcggtgtact actgcgcgac cggaaaccca  300
tactacacca atggattcaa tagctgggga cagggtactc ttgtgacggt gtccagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtggcc accggcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtat  840
gtggacggcg tggaggtgca taatgccaag acaaagccgc gggaggagca gtacaacagc  900
acgtaccgtg tggtcagcgt cctcaccgtc ctgcaccaag actggctgaa tggcaaggag  960
tacaagtgcg ccgtctccaa caaagccctc ccagcccccca tcgagaaaac catctccaaa  1020
gccaaagggc agccccgaga accacaggtg tacaccctgc ccccatcccg ggaggagatg  1080
```

```
accgacaacc aagtcagcct gacctgcctg gtcaaaggct tctatcccag cgacatcgcc  1140
gtggagtggg agagcaatgg gcagccggag aacaactaca agaccacgcc tcccgtgctg  1200
atgtccgacg gctccttctt cctcgcctcc aagctcaccg tggacaagag caggtggcag  1260
caggggaacg tcttctcatg ctccgtgatg catgaggctc tgcacaacca ctacacgcag  1320
aagagcctct ccctgtctcc gggcaaa                                      1347

SEQ ID NO: 35          moltype = AA  length = 330
FEATURE                Location/Qualifiers
source                 1..330
                       mol_type = protein
                       organism = synthetic construct
VARIANT                205
                       note = X is K or A
SEQUENCE: 35
ASTKGPSVFP LAPCSKSTSG GTAALGCLVK DYFPEPVTVS WNSGALTSGV HTFPAVLQSS  60
GLYSLSSVVT VPSSSLGTQT YICNVNHKPS NTKVDKRVEP DSGDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCXVSNKA LPAPIEKTIS KAKGQPRRPR VYTLPPSREE  240
MTKNQVSLVC LVKGFYPSDI AVEWESNGQP ENNYKTTPPV LDSDGSFFLY SVLTVDKSRW  300
QQGNVFSCSV MHEALHNHYT QKSLSLSPGK                                   330

SEQ ID NO: 36          moltype = AA  length = 330
FEATURE                Location/Qualifiers
source                 1..330
                       mol_type = protein
                       organism = synthetic construct
VARIANT                205
                       note = X is K or A
SEQUENCE: 36
ASTKGPSVFP LAPSSKSTSG GTAALGCLVK DYFPEPVTVS WNSGALTSGV ATGPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCXVSNKA LPAPIEKTIS KAKGQPREPQ VYTLPPSREE  240
MTDNQVSLTC LVKGFYPSDI AVEWESNGQP ENNYKTTPPV LMSDGSFFLA SKLTVDKSRW  300
QQGNVFSCSV MHEALHNHYT QKSLSLSPGK                                   330

SEQ ID NO: 37          moltype = AA  length = 453
FEATURE                Location/Qualifiers
source                 1..453
                       mol_type = protein
                       organism = synthetic construct
VARIANT                328
                       note = X is K or A
SEQUENCE: 37
QVQLVQSGAE VKKPGASVKV SCKASGYTFT GYYMHWVRYA PGQGLEWMGW INPNSGDTNY  60
AQKFQGRVTM TRDTSISTAY MELSRLRSDD TAVYYCAREG DSSGWHGGWF DPWGRGTLVT  120
VSSASTKGPS VFPLAPCSKS TSGGTAALGC LVKDYFPEPV TVSWNSGALT SGVHTFPAVL  180
QSSGLYSLSS VVTVPSSSLG TQTYICNVNH KPSNTKVDKR VEPDSGDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCXVS NKALPAPIEK TISKAKGQPR RPRVYTLPPS  360
REEMTKNQVS LVCLVKGFYP SDIAVEWESN GQPENNYKTT PPVLDSDGSF FLYSVLTVDK  420
SRWQQGNVFS CSVMHEALHN HYTQKSLSLS PGK                                453

SEQ ID NO: 38          moltype = AA  length = 449
FEATURE                Location/Qualifiers
source                 1..449
                       mol_type = protein
                       organism = synthetic construct
VARIANT                324
                       note = X is K or A
SEQUENCE: 38
QVQLVQSGAE VKKPGASVKV SCKVSGYSLS KYDMSWVRKA PGKGLEWMGI IYTSGYTDYA  60
QEFQGRVTMT EDTSTDTAYM ELSSLRSEDT AVYYCATGNP YYTNGFNSWG QGTLVTVSSA  120
STKGPSVFPL APSSKSTSGG TAALGCLVKD YFPEPVTVSW NSGALTSGVA TGPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCXVSNKAL PAPIEKTISK AKGQPREPQV YTLPPSREEM  360
TDNQVSLTCL VKGFYPSDIA VEWESNGQPE NNYKTTPPVL MSDGSFFLAS KLTVDKSRWQ  420
QGNVFSCSVM HEALHNHYTQ KSLSLSPGK                                    449

SEQ ID NO: 39          moltype = AA  length = 288
FEATURE                Location/Qualifiers
source                 1..288
                       mol_type = protein
                       organism = Homo sapiens
SEQUENCE: 39
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
```

-continued

```
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL              288

SEQ ID NO: 40          moltype = AA  length = 151
FEATURE                Location/Qualifiers
source                 1..151
                       mol_type = protein
                       organism = synthetic construct
SEQUENCE: 40
LDSPDRPWNP PTFSPALLVV TEGDNATFTC SFSNTSESFV LNWYRMSPSN QTDKLAAFPE  60
DRSQPGQDCR FRVTQLPNGR DFHMSVVRAR RNDSGTYLCG AISLAPKAQI KESLRAELRV  120
TERRAEVPTA HPSPSPRPAG QFQHHHHHHH H                                151

SEQ ID NO: 41          moltype = AA  length = 525
FEATURE                Location/Qualifiers
source                 1..525
                       mol_type = protein
                       organism = Homo sapiens
SEQUENCE: 41
MWEAQFLGLL FLQPLWVAPV KPLQPGAEVP VVWAQEGAPA QLPCSPTIPL QDLSLLRRAG  60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDWVILNCS FSRPDRPASV HWFRNRGQGR VPVRESPHHH LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL LLFLILGVLS LLLLVTGAFG FHLWRRQWRP  480
RRFSALEQGI HPPQAQSKIE ELEQEPEPEP EPEPEPEPEP EPEQL                 525

SEQ ID NO: 42          moltype = AA  length = 438
FEATURE                Location/Qualifiers
source                 1..438
                       mol_type = protein
                       organism = synthetic construct
SEQUENCE: 42
LQPGAEVPVV WAQEGAPAQL PCSPTIPLQD LSLLRRAGVT WQHQPDSGPP AAAPGHPLAP  60
GPHPAAPSSW GPRPRRYTVL SVGPGGLRSG RLPLQPRVQL DERGRQRGDF SLWLRPARRA  120
DAGEYRAAVH LRDRALSCRL RLRLGQASMT ASPPGSLRAS DWVILNCSFS RPDRPASVHW  180
FRNRGQGRVP VRESPHHHLA ESFLFLPQVS PMDSGPWGCI LTYRDGFNVS IMYNLTVLGL  240
EPPTPLTVYA GAGSRVGLPC RLPAGVGTRS FLTAKWTPPG GGPDLLVTGD NGDFTLRLED  300
VSQAQAGTYT CHIHLQEQQL NATVTLAIIT VTPKSFGSPG SLGKLLCEVT PVSGQERFVW  360
SSLDTPSQRS FSGPWLEAQE AQLLSQPWQC QLYQGERLLG AAVYFTELSS PGAQRSGRAP  420
GALPAGHGGG GSHHHHHH                                               438

SEQ ID NO: 43          moltype = AA  length = 461
FEATURE                Location/Qualifiers
source                 1..461
                       mol_type = protein
                       organism = synthetic construct
SEQUENCE: 43
MWEAQFLGLL FLQPLWVAPV KPPQPGAEIS VVWAQEGAPA QLPCSPTIPL QDLSLLRRAG  60
VTWQHQPDSG PPAPAPGHPP VPGHRPAAPY SWGPRPRRYT VLSVGPGGLR SGRLPLQPRV  120
QLDERGRQRG DFSLWLRPAR RADAGEYRAT VHLRDRALSC RLRLRVGQAS MTASPPGSLR  180
TSDWVILNCS FSRPDRPASV HWFRSRGQGR VPVQGSPHHH LAESFLFLPH VGPMDSGLWG  240
CILTYRDGFN VSIMYNLTVL GLEPATPLTV YAGAGSRVEL PCRLPPAVGT QSFLTAKWAP  300
PGGGPDLLVA GDNGDFTLRL EDVSQAQAGT YICHIRLQGQ QLNATVTLAI ITVTPKSFGS  360
PGSLGKLLCE VTPASGQEHF VWSPLNTPSQ RSFSGPWLEA QEAQLLSQPW QCQLHQGERL  420
LGAAVYFTEL SSPGAQRSGR APGALRAGHA AAHHHHHHSG S                     461
```